US008519109B2

(12) United States Patent
Huang et al.

(10) Patent No.: US 8,519,109 B2
(45) Date of Patent: Aug. 27, 2013

(54) TUMOUR REJECTION ANTIGENS

(75) Inventors: Lan-Qing Huang, Baltimore, MD (US); Aline van Pel, Brussels (BE); Francis Brasseur, Brussels (BE); Etienne De Plaen, Brussels (BE); Thierry Boon-Falleur, Brussels (BE)

(73) Assignee: Ludwig Institute for Cancer Research Ltd., New York, NY (US)

( * ) Notice: Subject to any disclaimer, the term of this patent is extended or adjusted under 35 U.S.C. 154(b) by 521 days.

(21) Appl. No.: 12/364,746

(22) Filed: Feb. 3, 2009

(65) Prior Publication Data

US 2009/0209034 A1    Aug. 20, 2009

Related U.S. Application Data

(62) Division of application No. 09/856,812, filed as application No. PCT/IB99/02018 on Nov. 26, 1999, now Pat. No. 7,547,439.

(30) Foreign Application Priority Data

Nov. 27, 1998    (GB) .................................. 9826143.1

(51) Int. Cl.
*C07H 21/04* (2006.01)
(52) U.S. Cl.
USPC ...................... 536/23.1; 536/23.4; 435/320.1
(58) Field of Classification Search
None
See application file for complete search history.

(56) References Cited

U.S. PATENT DOCUMENTS

| 5,686,068 A | 11/1997 | Melief et al. |
| 5,908,778 A * | 6/1999 | Rimoldi et al. ............ 435/320.1 |
| 5,912,143 A | 6/1999 | Bandman et al. |
| 6,682,731 B1 | 1/2004 | Townsend et al. |

FOREIGN PATENT DOCUMENTS

| WO | WO 92/20356 A | 11/1992 |
| WO | WO 94/20127 A1 | 9/1994 |
| WO | WO 95/25530 A | 9/1995 |
| WO | WO 95/25740 A1 | 9/1995 |
| WO | WO 98/14463 A | 4/1998 |
| WO | WO 99/45954 A | 9/1999 |
| WO | WO 99/54738 A | 10/1999 |
| WO | WO 99/61916 A | 12/1999 |

OTHER PUBLICATIONS

SCORE sequence search results, issued patent database, "20110313_112026_us-12-364-746a-3.rni" Mar. 13, 2011.*
Chen, Yao-Tseng et al., "Identification of multiple cancer/testis antigens by allogeneic antibody screening of a melanoma cell line library," *Proc. Natl. Acad. Sci. USA* Jun. 1998; 95:6919-6923.
Coulie, P.G., "Antigens Recognized on Human Tumors by Cytolytic T Lymphocytes: Towards Vaccination?" *Stem Cells* 1995; 13(4):393-403.
Dabovic, B. et al., "A family of rapidly evolving genes from the sex reversal critical region in Xp21," *Mammalian Genome* 1995; 6:571-580.
De Plaen, Etienne et al., "Structure, chromosomal localization, and expression of 12 genes of the MAGE family," *Immunogenetics* 1994; 40:360-369.
Gaugler, Beatrice et al., "Human Gene MAGE-3 Codes for an Antigen Recognized on a Melanoma by Autologous Cytolytic T Lymphocytes," *J. Exp. Med.* 1994; 179:921-930.
Gilbert, Sarah C. et al., "A protein particle vaccine containing multiple malaria epitopes," *Nature Biotechnology* Nov. 1997; 15:1280-1284.
Haas, Gilbert G. et al., "Distribution of Human Leukocyte Antigen-ABC and -D/DR Antigens in the Unfixed Human Testis," *American Journal of Reproductive Immunology and Microbiology* 1988; 18:47-51.
Hu, Xueyou et al., "Enhancements of Cytolytic T Lymphocyte Precursor Frequency in Melanoma Patients following Immunization with the MAGE-1 Peptide Loaded Antigen Presenting Cell-based Vaccine," *Cancer Research* Jun. 1, 1996; 56:2479-2483.
Huang, Lan-Qing et al., "Cytolytic T Lymphocytes Recognize an Antigen Encoded by MAGE-A10 on a Human Melanoma," *The Journal of Immunology* 1999; 162:6849-6854.
Lucas, Sophie et al., "Identification of a New Mage Gene with Tumor-specific Expression by Representational Difference Analysis," *Cancer Research* Feb. 15, 1998; 58:743-752.
Lurquin, Christophe et al., "Two Members of the Human MAGEB Gene Family Located in Xp21.3 Are Expressed in Tumors of Various Histological Origins," *Genomics* 1997; 46:397-408.
Marchand et al., "Tumor regression responses in melanoma patients treated with a peptide encoded by gene Mage-3," *Int. J. Cancer* 1995; 63:883-885.
Mukherji, Bijay et al., "Induction of antigen-specific cytolytic T cells in situ in human melanoma by immunization with synthetic peptide-pulsed autologous antigen presenting cells," *Proc. Natl. Acad. Sci. USA* Aug. 1995; 92:8078-8082.
Muscatelli, F. et al., "Isolation and characterization of a MAGE gene family in the Xp21.3 region," *Proc. Natl. Acad. Sci. USA* May 1995; 92:4987-4991.
Nestle, Frank O. et al., "Vaccination of melanoma patients with peptide- or tumor lysate-pulsed dendritic cells," *Nature Medicine* Mar. 1998; 4(3):328-332.
Rammensee, Hans-Georg et al., "MHC ligands and peptide motifs: first listing," *Immunogenetics* 1995; 41:178-228.
Rimoldi, Donata et al., "cDNA and Protein Characterization of Human MAGE-10," *Int. J. Cancer* 1999; 82:901-907.
Tam, James P. et al., "Incorporation of T and B Epitopes of the Circumsporozoite Protein in a Chemically Defined Synthetic Vaccine Against Malaria," *J. Exp. Med.* Jan. 1990; 171:299-306.
Thomson, Scott A. et al., "Minimal epitopes expressed in a recombinant polyepitope protein are processed and presented to CD8+ cytotoxic T cells: Implications for vaccine design," *Proc. Natl. Acad. Sci. USA* Jun. 1995; 92:5845-5849.

(Continued)

*Primary Examiner* — Laura B Goddard
(74) *Attorney, Agent, or Firm* — Wolf, Greenfield & Sacks, P.C.

(57) ABSTRACT

Polypeptides comprising an unbroken sequence of amino acids from SEQ. ID. NO. 1 or 2, with an ability to complex with a major histocompatibility complex molecule type HLA-A2, and preferably HLA-A2.1.

12 Claims, 16 Drawing Sheets

(56) References Cited

OTHER PUBLICATIONS

Traversari, Catia et al., "A Nonapeptide Encoded by Human Gene MAGE-1 is Recognized on HLA-A1 by Cytolytic T Lymphocytes Directed against Tumor Antigen MZ2-E," *J. Exp. Med.* Nov. 1992; 176:1453-1457.
Uyttenhove, Catherine et al., "The Expression of Mouse Gene P1A in Testis Does Not Prevent Safe Induction of Cytolytic T Cells Against a P1A-Encoded Tumor Antigen," *Int. J. Cancer* 1997; 70:349-356.
Van Den Eynde, B. et al., "Presence on a Human Melanoma of Multiple Antigens Recognized by Autologous CTL," *Int. J. Cancer* 1989; 44:634-640.
Van Der Bruggen, Pierre et al., "Autologous cytolytic T lymphocytes recognize a MAGE-1 nonapeptide on melanomas expressing HLA-Cw*1601*," *Eur. J. Immunol.* 1994; 24:2134-2140.
Van Der Bruggen, P. et al., "A Gene Encoding an Antigen Recognized by Cytolytic T Lymphocytes on a Human Melanoma," *Science* Dec. 13, 1991; 254:1643-1647.
Van Den Eynde, Benoit J. et al., "T cell defined tumor antigens," *Current Opinion in Immunology* 1997; 9:684-693.
Valmori, D. et al., "Frequent cytolytic T-cell responses to peptide MAGE-A10$_{254-262}$ in melanoma," *Cancer Research* 2001; 61:509-512.
Okada, K. et al., "A study of some new and useful n-terminal group sin mass spectrometry of peptides. The use of 3-hydroxyalkanoyl and unsaturated acyl groups," *Tetrahedron.* 1974; 30:1175-1185.
Kirkin et al., *APMIS* 1998; 106:665-676.
Bowie et al., *Science* 1990; 257:1306-1310.
Visseren et al., *Intl J Cancer* 1997; 73(1):125-30.
Stites et al., *Medical Immunology* 1997; 9$^{th}$ ed., Appleton & Large, Stamford, Connecticut, figure 3-9 on p. 51, pp. 50-51, 118-119, 130.
Herbert et al., *The Dictionary of Immunology*, Academic Press, 4$^{th}$ edition, 1995, p. 58.
Greenspan et al., *Nature Biotechnology* 1999; 7:936-937.
Yokota, J. et al., *Oncogene* 1988; 3:471-475.
Zimmer, *Cell Motility and the Cytoskeleton* 1991; 20:325-337.
Hell et al., *Laboratory Investigation* 1995; 73:492-496.
Guo et al., *Journal of Pharmacology and Experimental Therapeutics* 2002; 300(1):206-212.
White et al., *Ann Rev Med* 2001; 52:125-145.
Smith, R.T. *Clin. Immunol.* 1994; 41(4):841-849.
Drexler, *Leukemia and Lymphoma* 1993; 9:1-25.
Embleton et al., *Immunol. Ser.* 1984; 23:181-207.
Hsu, *Tissue Culture Methods and Applications*, Kruse and Patterson, eds., 1973, Academic Press, NY, see Abstract, p. 764.
Tian et al., *Physiol Genomics* 2004; 17:170-182.
Van Dyke et al., *Cancer Genetics and Gytogenetics* 2003; 241:137-141.
Zaslav et al., *Amer J Medical Genetics* 2002; 174-176.
Kunkel et al., *Neurooncology* 2001; 3(2):82-88.
Bergmann et al., *J. Virol.* 1994; 68(8):5306-5310.
Eisenlohr et al., *J. Exp. Med.* 1992; 175:481-487.
Shastri et al., *J. Immunol.* 1995; 155:4339-4346.
Guo et al., *Nature* 1992; 360:364-366.
MPSRCH search report 2006, us-09-856-812b-1.olig.rai, pp. 1-2.
MPSRCH search report 2006, us-09-856-812b-1_copy_254-262.olig.rai, pp. 1-2.
MPSRCH search report 2006, us-09-856-812b-1.olig_sz9.rai, p. 3.
MPSRCH search result 2007, us.09.856.812.1.oligo.sz9.Rag, result 3, pp. 1-2.
MPSRCH search result 2007, us.09.856.812b.48.rag, pp. 1-2.
Registry No. 53665-55-7 and Search Report 2006, pp. 1-2.

\* cited by examiner

Sequence cotransfected with HLA-A2.1
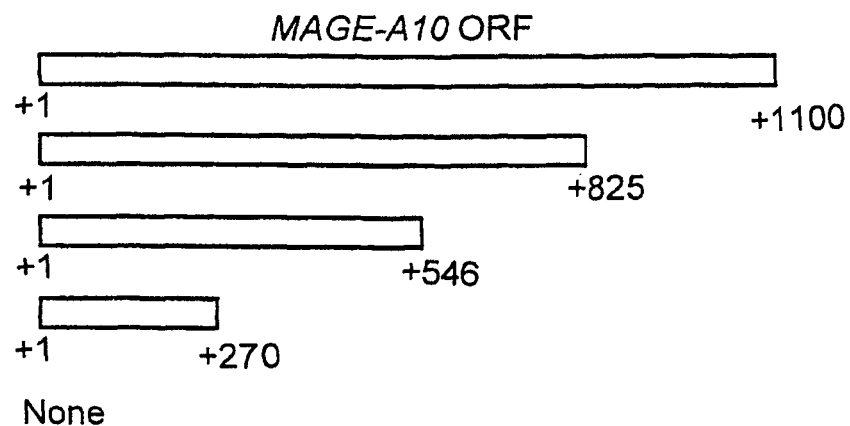
None
TNF released by CTL 447A/5 (pg/ml)
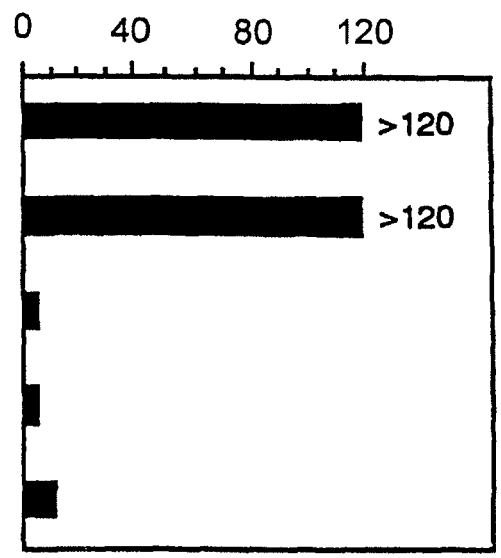
Fig. 3

Peptide concentration (nM)

● CMLLVFGIDV(182 – 191)
▲ MLLVFGIDV(183 – 191)

Peptide concentration (nM)

● GLYDGMEHL(254 – 262)
■ GLYDGMEHLI(254 – 263)

□ GLYDGREHS (No Ab)
■ GLYDGREHS (MA2.1)
◇ GLYDGREHSV (No Ab)
◆ GLYDGREHSV (MA2.1)

SEQ ID NO. 1

MPRAPKRQRCMPEEDLQSQSETQGLEGAQAPLAVEEDASSSTSTSSSFPSSFPSSSSSSSSSCYPLIPS
TPEEVSADDETPNPPQSAQIACSSPSVVASLPLDQSDEGSSSQKEESPSTLQVLPDSESLPRSEIDEKV
TDLVQFLLFKYQMKEPITKAEILESVIKNYEDHFPLLFSEASECMLLVFGIDVKEVDPTGHSFVLVTSL
GLTYDGMLSDVQSMPKTGILILILSIIFIEGYCTPEEVIWEALNMMGLYDGMEHLIYGEPRKLLTQDWV
QENYLEYRQVPGSDPARYEFLWGPRAHAEIRKMSLLKFLAKVNGSDPRSFPLWYEEALKDEEERAQDRI
ATTDDTTAMASASSSATGSFSYPE

Fig. 7

SEQ ID NO. 2

MLLGQKSQRYKAEEGLQAQGEAPGLMDVQIPTAEEQKAASSSSTLIMGTLEEVTDSGSPSPPQSPEGAS
SSLTVTDSTLWSQSDEGSSSNEEEGPSTSPDPAHLESLFREALDEKVAELVRFLLRKYQIKEPVTKAEM
LESVIKNYKNHFPDIFSKASECMQVIFGIDVKEVDPAGHSYILVTCLGLSYDGLLGDDQSTPKTGLLII
VLGMILMEGSRAPEEAIWEALSVMGAV

SEQ ID NO. 3

```
   1 cagggagatg gtggctttgg cgtgcaagac ccatacacga ttcagcagga gggaaaggct
  61 gggctgtcgg gagtaaatct gaatacctgg aggacaccca aataaaggaa gtccccgtct
 121 tgtcccctc ccctgcccac caccccccc ccccgcca aatgtctgct ccttctgtca
 181 gctttgggaa tcccatgcag gtgtgatcgt gtggtgcccc tccccacttc tgcctgccgg
 241 gtctcaggga ggtgaggacc ttggtctgag ggttgctaag aagttattac agggttccac
 301 acttggtcaa cagagggagg agtcccagaa tctgcaggac ccaagggggtg cccccttagt
 361 gaggactgga ggtacctgca gcccagaaag aagggatgtc acagagtctg gctgtccct
 421 gttcttagct ctgagggac ctgatcagga ttggcactaa gtggcaagct caattttacc
 481 acaggcagga agatgaggaa ccctcaggga aatggagttt tggtgtaaag gggagatatc
 541 agccctggac accccacagg gatgacagga tgtggctcct tcttactttt gttttggaat
 601 ctcaggagg tgagaacctt gctctcagag ggtgactcaa gtcaacacag ggaacccctc
 661 ttttctacag acacagtggg tcgcaggatc tgacaagagt ccaggtaagg aacctgaggg
 721 aaatctgagg gtaccccag cccataacac agatgggtc cccacagaaa tctgccatga
 781 ccctactgtc actctggaga acccagtcag ggctgtccgc tgagtctccc tgtcttatac
 841 aaggatcact ggtctctggg agggagaggt gttggtctaa gggagctgca ctcgggtcag
 901 cagagggagg gtcccagacc ctgccaggag tcaaggtgag gactgagggg acaccattct
 961 ccaaacgcac aggactcagc cccaccctac cccttctgtc agccacggga attcatgggg
1021 aactgggggt agatggactc ccctcacttc ctctttccat gtctcctgga ggtaggacct
1081 tggtttaagg aagtggcctc agatcaacaa agggagggtc ccaggctgta tcaggcatca
1141 agaagaggac caagcaggct cctcaccca gtacacatgg acccagctga atatggccac
1201 ctcttgctgt cttttctggg aggacctctg cagttgtggc cagatgtggg tcccctcatg
1261 tcttctattt cgtatcaggg atgtaagctt ttgatctgag agtttcttag accagcaaag
1321 gagcagggtc taggcttttc caggagaaag gtgagagccc cacgtgagca cagaggctcc
1381 ccaccccagg gtagtgggga actcacagag tccagcccac cctcctgaca acactgggag
1441 gctgggggctg tgcttgcagc ctgaaccctg agggcccctc aattcctctt tcaggagctc
1501 cagggactgt gaggtgaggc cttggtctaa ggcagtgttt tcaggtcaca gagcagaaag
1561 ggcccagaca gtgccaggag tcaaggtgag gtgcatgccc tgaatgtgta ccaagggccc
1621 cacctgctcc aggacaaagt ggaccccact gcatcagctc cacctaccct actgtcagtc
1681 ctggagcctt ggcctctgcc ggctgcatcc tgaggagcca tctctcactt ccttcttcag
1741 gttctcaggg gacagggaga gcaagaggtc aagagctgtg ggacaccaca gagcagcact
1801 gaaggagaag acctgtaagt tggcctttgt tagaacctcc agggtgtggt tctcagctgt
1861 ggccacttac accctccctc tctccccagg cctgtgggtc cccatcgccc aagtcctgcc
1921 cacactccca cctgctaccc tgatcagagt catcatgcct cgagctccaa agcgtcagcg
1981 ctgcatgcct gaagaagatc ttcaatccca aagtgagaca cagggcctcg agggtgcaca
2041 ggctcccctg gctgtggagg aggatgcttc atcatccact tccaccagct cctctttcc
2101 atcctctttt ccctcctcct cctcttcctc ctcctcctcc tgctatcctc taataccaag
2161 cacccagag gaggtttctg ctgatgatga gacaccaaat cctcccagaa gtgctcagat
2221 agcctgctcc tccccctcgg tcgttgcttc ccttccatta gatcaatctg atgagggctc
2281 cagcagccaa aaggaggaga gtccaagcac cctacaggtc ctgccagaca gtgagtcttt
2341 acccagaagt gagatagatg aaaaggtgac tgatttggtg cagtttctgc tcttcaagta
2401 tcaaatgaag gagccgatca caaaggcaga aatactggag agtgtcataa aaaattatga
2461 agaccacttc cctttgttgt ttagtgaagc ctccgagtgc atgctgctgg tctttggcat
2521 tgatgtaaag gaagtggatc ccactggcca ctcctttgtc cttgtcacct ccctgggcct
2581 cacctatgat gggatgctga gtgatgtcca gagcatgccc aagactggca ttctcatact
2641 tatcctaagc ataatcttca tagagggcta ctgcacccct gaggaggtca tctgggaagc
2701 actgaatatg atgggctgt atgatgggat ggagcacctc atttatgggg agcccaggaa
2761 gctgctcacc caagattggt gcaggaaaa ctacctggag taccggcagg tgcctggcag
2821 tgatcctgca cggtatgagt ttctgtgggg tccaagggct catgctgaaa ttaggaagat
2881 gagtctcctg aaattttgg ccaaggtaaa tgggagtgat ccaagatcct tcccactgtg
2941 gtatgaggag gctttgaaag atgaggaaga gagagcccag gacagaattg ccaccacaga
```

```
3001 tgatactact gccatggcca gtgcaagttc tagcgctaca ggtagcttct cctaccctga
3061 ataaagtaag acagattctt cactgtgttt taaaaggcaa gtcaaatacc acatgatttt
3121 actcatatgt ggaatctaaa aaaaaaaaaa aaaaaagttg gtatcatgga agtagagagt
3181 agagcagtag ttacattaca attaaatagg aggaataagt tctagtgttc tattgcacag
3241 taggatgact atagttaaca ttaagatatt gtatattaca aaacagctag aaggaaggct
3301 tttcaatatt gtcaccaaaa agaaatgata aatgcatgag gtgatggata cactacctga
3361 tttgatcatt atactacata tacatgaatc agaacatcaa attgtacctc ataaatatct
3421 acaattacat gtcagttttt gtttatgttt ttgttttttt ttaatttatg aaaacaaatg
3481 agaatggaaa tcaatgatgt atgtggtgga
```

Fig. 9 continued

SEQ ID NO. 4

Fig. 10a

| | | | | | |
|---|---|---|---|---|---|
| TCCGGGGTCG | CTCGAGCCGG | CCGGGACTCG | GGGATCASAA | GTAACGGCGG | 50 |
| YYMKYGTKCT | GAGGGACAGG | CTTGAGATCG | GCTGAAGAGA | GCGGGCCCAG | 100 |
| GCTCTGTGAG | GAGGCAAGGG | AGGTGAGAAC | CTTGCTCTCA | GAGGGTGACT | 150 |
| CAAGTCAACA | CAGGGAACCC | CTCTTTCTA | CAGACACAGT | GGGTCGCAGG | 200 |
| ATCTGACAAG | AGTCCAGGTT | CTCAGGGGAC | AGGGAGAGCA | AGAGGTCAAG | 250 |
| AGCTGTGGGA | CACCACAGAG | CAGCACTGAA | GGAGAAGACC | TGCCTGTGGG | 300 |
| TCCCCATCGC | CCAAGTCCTG | CCCACACTCC | CACCTGCTAC | CCTGATCAGA | 350 |
| GTCATCATGC | CTCGAGCTCC | AAAGCGTCAG | CGCTGCATGC | CTGAAGAAGA | 400 |
| TCTTCAATCC | CAAAGTGAGA | CACAGGGCCT | CGAGGGTGCA | CAGGCTCCCC | 450 |
| TGGCTGTGGA | GGAGGATGCT | TCATCATCCA | CTTCCACCAG | CTCCTCTTTT | 500 |
| CCATCCTCTT | TTCCCTCCTC | CTCCTCTTCC | TCCTCCTCCT | CCTGCTATCC | 550 |
| TCTAATACCA | AGCACCCCAG | AGGAGGTTTC | TGCTGATGAT | GAGACACCAA | 600 |
| ATCCTCCCCA | GAGTGCTCAG | ATAGCCTGCT | CCTCCCCCTC | GGTCGTTGCT | 650 |
| TCCCTTCCAT | TAGATCAATC | TGATGAGGGC | TCCAGCAGCC | AAAAGGAGGA | 700 |
| GAGTCCAAGC | ACCCTACAGG | TCCTGCCAGA | CAGTGAGTCT | TTACCCAGAA | 750 |
| GTGAGATAGA | TGAAAAGGTG | ACTGATTTGG | TGCAGTTTCT | GCTCTTCAAG | 800 |
| TATCAAATGA | AGGAGCCGAT | CACAAAGGCA | GAAATACTGG | AGAGTGTCAT | 850 |
| AAAAAATTAT | GAAGACCACT | TCCCTTTGTT | GTTTAGTGAA | GCCTCCGAGT | 900 |
| GCATGCTGCT | GGTCTTTGGC | ATTGATGTAA | AGGAAGTGGA | TCCCACTGGC | 950 |
| CACTCCTTTG | TCCTTGTCAC | CTCCCTGGGC | CTCACCTATG | ATGGGATGCT | 1000 |
| GAGTGATGTC | CAGAGCATGC | CCAAGACTGG | CATTCTCATA | CTTATCCTAA | 1050 |
| GCATAATCTT | CATAGAGGGC | TACTGCACCC | CTGAGGAGGT | CATCTGGGAA | 1100 |
| GCACTGAATA | TGATGGGCT | GTATGATGGG | ATGGAGCACC | TCATTTATGG | 1150 |
| GGAGCCCAGG | AAGCTGCTCA | CCCAAGATTG | GGTGCAGGAA | AACTACCTGG | 1200 |
| AGTACCGGCA | GGTGCCTGGC | AGTGATCCTG | CACGGTATGA | GTTTCTGTGG | 1250 |
| GGTCCAAGGG | CTCATGCTGA | AATTAGGAAG | ATGAGTCTCC | TGAAATTTTT | 1300 |
| GGCCAAGGTA | AATGGGAGTG | ATCCAAGATC | CTTCCCACTG | TGGTATGAGG | 1350 |
| AGGCTTTGAA | AGATGAGGAA | GAGAGAGCCC | AGGACAGAAT | TGCCACCACA | 1400 |
| GATGATACTA | CTGCCATGGC | CAGTGCAAGT | TCTAGCGCTA | CAGGTAGCTT | 1450 |
| CTCCTACCCT | GAATAAAGTA | AGACAGATTC | TTCACTGTGT | TTTAAAAGGC | 1500 |
| AAGTCAAATA | CCACATGATT | TTACTCATAT | GTGGAATCTA | AAAAAAAAAA | 1550 |
| AAAAAAAAGT | TGGTATCATG | GAAGTAGAGA | GTAGAGCAGT | AGTTACATTA | 1600 |
| CAATTAAATA | GGAGGAATAA | GTTCTAGTGT | TCTATTGCAC | AGTAGGATGA | 1650 |
| CTATAGTTAA | CATTAAGATA | TTGTATATTA | CAAAACAGCT | AGAAGGAAGG | 1700 |
| CTTTTCAATA | TTGTCACCAA | AAAGAAATGA | TAAATGCATG | AGGTGATGGA | 1750 |

| | | | | | |
|---|---|---|---|---|---|
| TACACTACCT | GATGTGATCA | TTATACTACA | TATACATGAA | TCAGAACATC | 1800 |
| AAATTGTACC | TCATAAATAT | CTACAATTAC | ATGTCAGTTT | TTGTTTATGT | 1850 |
| TTTTGTTTTT | TTTTAATTTA | TGAAAACAAA | TGAGAATGGA | AATCAATGAT | 1900 |
| GTATGTGGTG | GAGGGCCAGG | CTGAGGCTGA | GGAAAATACA | GTGCATAACA | 1950 |
| TCTTTGTCTT | ACTGTTTTCT | TTGGATAACC | TGGGGACTTC | TTTTCTTTTC | 2000 |
| TTCTTGGTAT | TTTATTTTCT | TTTTCTTCTT | CTTCTTTTTT | TTTTTTAACA | 2050 |
| AAGTCTCACT | CTATTGCTCT | GGCAGGAGTG | CAGTGGTGCA | GTCTCGGCTC | 2100 |
| ACTGCAACTT | CCGCCTCCTG | GGTTCAAGCG | ATTCTCCTGC | CTCAGTCTCC | 2150 |
| TGAGTAGCTG | GGATTACAAG | TGTGCACCAC | CATACCCGGC | TAATTTTGTA | 2200 |
| TTTTTTAGTA | GAGATGGGGT | TTCACCATGT | TGGCCAGGCT | GGTCTCAAAC | 2250 |
| TCCTGACCTC | AGGTAATCTG | CCCGCCTCAG | CCTCCCAAAG | TGCTGGGATA | 2300 |
| ACAGGTGTGA | GCCCACTGCA | CCCCAGCCTC | TTCTTGGTAT | TTTAAAATGT | 2350 |
| TGTTACTTTT | ACTAGAATGT | TTATGAGCTT | CAGAATCTAA | GGTCACACGT | 2400 |
| TCGTTTCTGT | TTATCCAGTT | TAAGAAACAG | TTTTGCTATT | TTGTAAAACA | 2450 |
| AATTGGGAAC | CCTTCCATCA | TATTTGTAAT | CTTTAATAAA | ATAACATGGA | 2500 |
| ATTGGAATAG | TAATTTTCTT | GGAAATATGA | AAAAATAGTA | AAATAGAGAA | 2550 |
| AATAATTTT | | | | | 2559 |

Fig. 10b

SEQ ID NO. 5

Fig. 11a

```
   1 agtctcagat cactggagag aggtgcccca gagcccttaa ggaggactca gcagacctcc
  61 catcatggcc taggaaacct gctcccactc tcaggtctgg gcacccaagg caggacagtg
 121 gggaagggat gtggccccca cactttctgg tagggggggcc tcaaggagat ggtggccttg
 181 gcatgcaaga cacatccacg gttcagcagg aaggaaaggg ccatgccttg tcgtggagta
 241 aatatgaata cctggatgac acccagacag agaaagaccc catgaaacct actacttctg
 301 tcagccgtgg gaatcccatg cagggttgtc catgtagtgc ctccttactt ctgcctcctg
 361 ggtctcaggg aggtagcaac ctgggtctga agggcgtcct cagctcagca gagggagcca
 421 cacctgttca acagagggac ggggtcacag gatctgcagg acccaagatg tgctcacttt
 481 gtgatgaatg ggggtactcc tggcctggaa agaagggacc ccacaaagtc tggctaactt
 541 tggttattat ctctggggga acccgatcaa gggtggccct aagtggagat ctcatctgta
 601 ctgtgggcag gaagttgggg aaacgcagga agataaggtc ttggtggtaa ggggagatgt
 661 ctgctcatat cagggtgttg tgggttgagg aagggcgggc tccatcaggg gaaagatgaa
 721 taacccctg aagaccttag aacccaccac tcaagaacaa gtagggacag atcctagtgt
 781 caccctgga caccaccc agtggtcatc agatgtggtg gctcctcatt tctctcttga
 841 gtctcaggga agtgaggacc ttgttctcag agggcaactc aggacaaaac agggaccccc
 901 atgtgggcaa cagactcagt ggtccaagaa tctaccaaga gtctaggtga caacactgag
 961 ggaagattga gggtaccctc gatggttctc ctagcaggca aaaaacagat gggggcccaa
1021 cagaaatctg cccggcctct tttgtcaccc ctgagcat gagcaggact atcagctgag
1081 gcccctgtgt tataccagac tcattggtct caggagaag aaggccttgg tctgagggca
1141 ctgcattcag gtcagcagag cgggggtcca aggccctgcc aggagtcagg gactcagagg
1201 acaccactca ccaaacacac aggaccgaac cccaccctgc accttctgtc agccatggga
1261 agtgcaggga aaggtgggtg gatggaatcc cctcatttgc tcttccagtg tctcctggag
1321 ataggtcctt ggattaagga agtggcctca ggtcagccca ggacacatgg gccccaatgt
1381 attttgtgta gctattgctt ttttctcacc ctaggacaga cacgtgggcc ccattgcatt
1441 ttgtgtagct attgctttt tcccaggagg ccttgggcat gtggggccag atgtgggtcc
1501 cttcatatcc ttgtcttcca tatcagggat ataaactctt gatctgaaag tttctcaggc
1561 cagcaaaagg gccagatcca ggccctgcca ggagaaagat gagggccctg aatgagcaca
1621 gaaaggacca tccacacaaa atagtgggga gctcacagag tcaggctcac cctcctgaca
1681 gcactggggt gctgggctg tgcttgcagt ctgcagcctg agttcccctc gatttatctt
1741 ctaggagctc caggaaccag gctgtgaggt cttggtctga ggcagtatct tcaatcacag
1801 agcataagag gcccaggcag tagtagcagt caagctgagg tggtgtttcc cctgtatgta
1861 taccagaggc ccctctggca tcagaacagc aggaaccca cagttcctgg ccctaccagc
1921 cctttgtca gtcctggagc cttggccttt gccaggaggc tgcaccctga gatgccctct
1981 caatttctcc ttcaggttcg cagagaacag gccagccagg aggtcaggag gccccagaga
2041 agcactgaag aagacctgta agtagacctt tgttagggca tccagggtgt agtaccccagc
2101 tgaggcctct cacacgcttc ctctctcccc aggcctgtgg gtctcaattg cccagctccg
2161 gcccacactc tcctgctgcc ctgacctgag tcatcatgct tcttgggcag aagagtcagc
2221 gctacaaggc tgaggaaggc cttcaggccc aaggagaggc accagggctt atggatgtgc
2281 agattcccac agctgaggag cagaaggctg catcctcctc ctctactctg atcatgggaa
2341 cccttgagga ggtgactgat tctggtcac caagtcctcc ccagagtcct gagggtgcct
2401 cctcttccct gactgtcacc gacagcactc tgtggagcca atccgatgag ggttccagca
2461 gcaatgaaga ggaggggcca agcacctccc cggacccagc tcacctggag tccctgttcc
2521 gggaagcact tgatgagaaa gtggctgagt tagttcgttt cctgctccgc aaatatcaaa
2581 ttaaggagcc ggtcacaaag gcagaaatgc ttgagagtgt catcaaaaat tacaagaacc
2641 actttcctga tatcttcagc aaagcctctg agtgcatgca ggtgatcttt ggcattgatg
2701 tgaaggaagt ggaccctgcc ggccactcct acatccttgt cacctgcctg ggcctctcct
2761 atgatggcct gctgggtgat gatcagagta cgcccaagac cggcctcctg ataatcgtcc
```

```
2821 tgggcatgat cttaatggag ggcagccgcg ccccggagga ggcaatctgg gaagcattga
2881 gtgtgatggg ggctgtatga tgggagggag cacagtgtct attggaagct caggaagctg
2941 ctcacccaag agtgggtgca ggagaactac ctggagtacc gccaggcgcc cggcagtgat
3001 cctgtgcgct acgagttcct gtggggtcca agggcccttg ctgaaaccag ctatgtgaaa
3061 gtcctggagc atgtggtcag ggtcaatgca agagttcgca tttcctaccc atccctgcat
3121 gaagaggctt tgggagagga gaaggagtt tgagcaggag ttgcagctag ggccagtggg
3181 gcaggttgtg ggagggcctg ggccagtgca cgttccaggg ccacatccac cactttccct
3241 gctctgttac atgaggccca ttcttcactc tgtgtttgaa gagagcagtc acagttctca
3301 gtagtgggga gcatgttggg tgtgagggaa cacagtgtgg accatctctc agttcctgtt
3361 ctattgggcg atttggaggt ttatctttgt ttccttttgg aattgttcca atgttccttc
3421 taatggatgg tgtaatgaac ttcaacattc attttatgta tgacagtaga cagacttact
3481 gcttttata tagtttagga gtaagagtct tgcttttcat ttatactggg aaacccatgt
3541 tatttcttga attcagacac tacaagagca gaggattaag gttttttag aaatgtgaaa
3601 caacatagca gtaaaataca tgagataaag acataaagaa attaaacaat agttaattct
3661 tgccttacct gtacctctta gtgtacccta tgtacctgaa tttgcttggc ttctttgaga
3721 atgaaattga attaaatatg aataaataag tccccctgct cactggctca ttttttccca
3781 aaatattcat tgagcttccg ctatttggaa ggccctgggt tagtattgga gatgctaca
```

Fig. 11b

SEQ ID NO. 6

```
GAGCTCCAGG AACCAGGCTG TGAGGTCTTG GTCTGAGGCA GTATCTTCAA        50
TCACAGAGCA TAAGAGGCCC AGGCAGTAGT AGCAGTCAAG CTGAGGTGGT       100
GTTTCCCCTG TATGTATACC AGAGGCCCCT CTGGCATCAG AACAGCAGGA       150
ACCCCACAGT TCCTGGCCCT ACCAGCCCTT TTGTCAGTCC TGGAGCCTTG       200
GCCTTTCCCA GGAGGCTGCA CCCTGAGATG CCCTCTCAAT TTCTCCTTCA       250
GGTTCGCAGA GAACAGGCCA GCCAGGAGGT CAGGAGGCCC CAGAGAAGCA       300
CTGAAGAAGA CCTGTAAGTA GACCTTTGTT AGGGCATCCA GGGTGTAGTA       350
CCCAGCTGAG GCCTCTCACA CGCTTCCTCT CTCCCCAGGC CTGTGGGTCT       400
CAATTGCCCA GCTCCGGCCC ACACTCTCCT GCTGCCCTGA CCTGAGTCAT       450
C                                                            451
ATG CTT CTT GGG CAG AAG AGT CAG CGC TAC AAG GCT GAG GAA      493
GGC CTT CAG GCC CAA GGA GAG GCA CCA GGG CTT ATG GAT GTG      535
CAG ATT CCC ACA GCT GAG GAG CAG AAG GCT GCA TCC TCC TCC      577
TCT ACT CTG ATC ATG GGA ACC CTT GAG GAG GTG ACT GAT TCT      619
GGG TCA CCA AGT CCT CCC CAG AGT CCT GAG GGT GCC TCC TCT      661
TCC CTC ACT GTC ACC GAC AGC ACT CTG TGG AGC CAA TCC GAT      703
GAG GGT TCC AGC AGC AAT GAA GAG GAG GGG CCA AGC ACC TCC      745
CCG GAC CCA GCT CAC CTG GAG TCC CTG TTC CGG GAA GCA CTT      787
GAT GAG AAA GTG GCT GAG TTA GTT CGT TTC CTC CTC CGC AAA      829
TAT CAA ATT AAG GAG CCG GTC ACA AAG GCA GAA ATG CTT GAG      871
AGT GTC ATC AAA AAT TAC AAG AAC CAC TTT CCT GAT ATC TTC      913
AGC AAA GCC TCT GAG TGC ATG CAG GTG ATC TTT GGC ATT GAT      955
GTG AAG GAA GTG GAC CCT GCC GGC CAC TCC TAC ATC CTT GTC      997
ACC TGC CTG GGC CTC TCC TAT GAT GGC CTC CTG GGT GAT GAT     1039
CAG AGT ACG CCC AAG ACC GGC CTC CTG ATA ATC GTC CTG GGC     1081
ATG ATC TTA ATG GAG GGC AGC CGC GCC CCG GAG GAG GCA ATC     1123
TGG GAA GCA TTC AGT GTG ATG GGG GCT GTA TGA                 1156
TGGGAGGGAG CACAGTGTCT ATTGGAAGCT CAGGAAGCTG CTCACCCAAG      1206
AGTGGGTGCA GGAGAACTAC CTGGAGTACC GCCAGGCGCC CGGCAGTGAT      1256
CCTGTGCGCT ACGAGTTCCT GTGGGGTCCA AGGGCCCTTG CTGAAACCAG      1306
CTATGTGAAA GTCCTGGAGC ATGTGGTCAG GGTCAATGCA AGAGTTCGCA      1356
TTTCCTACCC ATCCCTGCAT GAAGAGGCTT TGGAGAGGA GAAAGGAGTT       1406
TGAGCAGGAG TTGCAGCTAG GGCCAGTGGG GCAGGTTGTG GGAGGGCCTG      1456
GGCCAGTGCA CGTTCCAGGG CCACATCCAC CACTTTCCCT GCTCTGTTAC      1506
ATGAGGCCCA TTCTTCACTC TCTGTTTGAA GAGAGCAGTC ACAGTTCTCA      1556
GTAGTGGGGA GCATGTTGGG TGTGAGGGAA CACAGTGTGG ACCATCTCTC      1606
AGTTCCTGTT CTATTGGGCG ATTTGGAGGT TTATCTTTGT TTCCTTTTGG      1656
AATTGTTCCA ATGTTCCTTC TAATGGATGG TGTAATGAAC TTCAACATTC      1706
ATTTTATGTA TGACAGTAGA CAGACTTACT GCTTTTTATA TAGTTTAGGA      1756
GTAAGAGTCT TGCTTTTCAT TTATACTGGG AAACCCATGT TATTTCTTGA      1806
ATTC                                                         1810
```

Fig. 12

SEQ ID NO. 7

```
ACCTGCTCCA GGACAAAGTG GACCCCACTG CATCAGCTCC ACCTACCCTA        50
CTGTCAGTCC TGGAGCCTTG GCCTCTGCCG GCTGCATCCT GAGGAGCCAT       100
CTCTCACTTC CTTCTTCAGG TTCTCAGGGG ACAGGGAGAG CAAGAGGTCA       150
AGAGCTGTGG GACACCACAG AGCAGCACTG AAGGAGAAGA CCTGTAAGTT       200
GGCCTTTGTT AGAACCTCCA GGGTGTGGTT CTCAGCTGTG GCCACTTACA       250
CCCTCCCTCT CTCCCCAGGC CTGTGGGTCC CCATCGCCCA AGTCCTGCCC       300
ACACTCCCAC CTGCTACCCT GATCAGAGTC ATC                         333
ATG CCT CGA GCT CCA AAG CGT CAG CGC TGC ATG CCT GAA GAA       375
GAT CTT CAA TCC CAA AGT GAG ACA CAG GGC CTC GAG GGT GCA       417
CAG GCT CCC CTG GCT GTG GAG GAG GAT GCT TCA TCA TCC ACT       459
TCC ACC AGC TCC TCT TTT CCA TCC TCT TTT CCC TCC TCC TCC       501
TCT TCC TCC TCC TCC TCC TGC TAT CCT CTA ATA CCA AGC ACC       543
CCA GAG GAG GTT TCT GCT GAT GAT GAG ACA CCA AAT CCT CCC       585
CAG AGT GCT CAG ATA GCC TGC TCC TCC CCC TCG GTC GTT GCT       627
TCC CTT CCA TTA GAT CAA TCT GAT GAG GGC TCC AGC AGC CAA       669
AAG GAG GAG AGT CCA AGC ACC CTA CAG GTC CTG CCA GAC AGT       711
GAG TCT TTA CCC AGA AGT GAG ATA GAT GAA AAG GTG ACT GAT       753
TTG GTG CAG TTT CTG CTC TTC AAG TAT CAA ATG AAG GAG CCG       795
ATC ACA AAG GCA GAA ATA CTG GAG AGT GTC ATA AAA AAT TAT       837
GAA GAC CAC TTC CCT TTG TTG TTT AGT GAA GCC TCC GAG TGC       879
ATG CTG CTG GTC TTT GGC ATT GAT GTA AAG GAA GTG GAT CC        920
```

Fig. 13

TUMOUR REJECTION ANTIGENS

RELATED APPLICATIONS

This application is a divisional of application Ser. No. 09/856,812, filed Sep. 7, 2001, now U.S. Pat. No. 7,547,439, which is a national stage application under 35 U.S.C. §371 of international application PCT/IB99/02018, filed Nov. 26, 1999, which was published under PCT Article 21(2) in English, the entire contents of each of which are incorporated by reference herein.

FIELD OF THE INVENTION

This invention relates to polypeptides and proteins expressed in tumour cells and to nucleic acid molecules coding for such polypeptides and proteins. The invention also relates to expression vectors and host cells for expressing such polypeptides and proteins, and to polypeptide-binding agents which selectively bind or are specific for such polypeptides or proteins. The invention further relates to methods of treating and diagnosing disease, preferably cancers, using such polypeptides, proteins, nucleic acids, polypeptide-binding agents, expression vectors or transformed host cells.

BACKGROUND OF THE INVENTION

The phenotypic changes which distinguish a tumour cell from its normal counterpart are often the result of one or more changes to the genome of the cell. The genes which are expressed in tumour cells, but not in normal counterparts, can be termed "tumour specific" or "tumour associated" genes. These tumour specific or associated genes can be markers for the tumour phenotype.

The process by which the mammalian immune system recognises and reacts to foreign or alien materials is a complex one. An important facet of the system is the response of cytolytic T lymphocytes (CTLs) or T cells. CTLs recognise and interact with complexes of cell surface molecules, referred to as human leukocyte antigens ("HLA"), or major histocompatibility complex molecules ("MHC" molecules), and other peptides derived from larger molecules from within the cells carrying the HLA/MHC complexes. See, in this regard, Male et al., Advanced Immunology (J. P. Lipincott Company, 1987), especially chapters 6-10, and C. A. Janeway et al. Immuno Biology third ed. (Current Biology Ltd. 1997). The interaction of T cells and complexes of HLA/peptide is restricted, requiring a T cell specific for a particular combination of an HLA molecule and a peptide. If a specific CTL is not present, there is no T cell response even if its partner complex is present. Similarly, there is no response if the specific complex is absent, but the CTL is present. The mechanism is involved in the immune system's response to foreign materials, in autoimmune pathologies, and in responses to cellular abnormalities. Much work has focused on the mechanisms by which proteins are processed into the HLA binding peptides. See, in this regard, Barinaga, Science 257:880, 1992; Fremont et al., Science 257:919, 1992; Matsumura et al., Science 257:927, 1992; Latron et al., Science 257: 964, 1992.

The mechanism by which T cells recognise cellular abnormalities has also been implicated in cancer. A number of families of genes which are processed into peptides that are presented as HLA/peptide complexes on the surface of tumour cells, with the result that the cells can be lysed by specific CTLs, have been discovered. These genes are said to code for "tumour rejection antigen precursors" or "TRAP" molecules, and the peptides derived therefrom that complex with HLA are referred to as "tumour rejection antigens" or "TRAs". Intensive efforts have been made in this field and a wealth of human tumour rejection antigens (both TRAPs and TRAs) which are recognised by T cells have been identified (Van den Eynde, B. J., and P. van der Bruggen, 1997, Curr. Opin. Immunol. 9:684.). Among them, a TRAP encoded by the gene MAGE-1 was initially defined by cultivating blood lymphocytes of patient MZ2 in the presence of a melanoma cell line derived from the same patient. A panel of CTL clones was generated by mixed lymphocyte-tumour cell culture (MLTC) techniques, and one of these clones recognised a nonapeptide TRA derived from the MAGE-1 TRAP, which is presented by HLA-A1 (van der Bruggen, P., C. et al., 1991, Science (Wash. D.C.). 254:1643-1647; Traversari, C., et al., 1992, J. Exp. Med. 176:1453-1457 and WO92/20356). It was found later that MAGE-1 belongs to a family of at least seventeen related genes, namely MAGE-1 to −12 (now named MAGE-A1 to -A12)(De Plaen, E., et al., 1994, Immunogenetics. 40:360-369.), MAGE-B1 to -B4 (Muscatelli, F., et al., 1995, Proc. Natl. Acad. Sci. USA. 92:4987-4991; Dabovic, B., et al., 1995, Mammalian Genome. 6:571-580; and Lurquin, C., et al., 1997, Genomics. 46:397-408), and MAGE-C1 (Lucas, S., et al., 1998, Cancer Res. 58:743-752).

Genes of this family are expressed in various tumours of different histological types, but are completely silent in normal tissues with the exception of testis and placenta (De Plaen, E., et al., 1994, Immunogenetics. 40:360-369; Dabovic, B., et al., 1995, Mammalian Genome. 6:571-580; Lurquin, C., et al., 1997, Genomics. 46:397-408; and Lucas, S., et al., 1998, Cancer Res. 58:743-752.). However, as testicular germ cells and placental trophoblasts do not express MHC class 1 molecules (Haas, G. G. Jr., et al., 1988, Am. J. Reprod. Immunol. Microbiol. 18:47-51.), gene expression in these tissues should not lead to antigen expression. Indeed, immunisation of male mice with an antigen encoded by mouse P1A gene, which has the same expression pattern as human MAGE gene, i.e., expressed in tumours, testis and placenta, but silent in other normal tissues, produced strong P1A-specific CTL responses that did not cause testis inflammation or alteration of fertility (Uyttenhove, C., C. et al., 1997, Int. J. Cancer. 70:349-356.). Antigens encoded by MAGE genes are, therefore, suitable candidates for vaccine-based immunotherapy of cancers and as markers for providing a means of identifying a cell as a so treatable tumour cell.

SUMMARY OF THE INVENTION

So far, however, it has only proven possible to identify TRAs encoded by MAGE-A1, -A3 and -A6 by using autologous CTLs derived from mixed lymphocyte-tumour cell cultures (MLTC) and previous gene expression assays have suggested that MAGE-A10 was expressed in tumours at a level that was too low to be sufficient for CTL recognition. All these CTLs were generated from only one patient, MZ2 (Traversari, C., et al., 1992, J. Exp. Med. 176:1453-1457; van der Bruggen, P., et al., 1994, Eur. J. Immunol. 24:2134-2140; Gaugler, B., et al., 1994, Exp. Med. 179:921-930; De Plaen, E., et al., 1994, Immunogenetics. 40:360-369; and P. van der Bruggen, unpublished data). However, the inventors have now been able to obtain autologous CTL clones from another melanoma patient, LB 1751, which recognize and have allowed the identification of hitherto unknown HLA-A2.1-presented TRAs encoded by MAGE-A10 and MAGE-A8.

Accordingly, the present invention provides a polypeptide comprising an unbroken sequence of amino acids from SEQ.

ID. NO. 1 (FIG. 7) or SEQ. ID. NO. 2 (FIG. 8) which has an ability to complex with an MHC molecule type HLA-A2, preferably HLA-A2.1. Polypeptides in accordance with the invention can comprise unbroken sequences of amino acids from SEQ. ID. NO. 1 or 2 which have an ability to elicit an immune response from human lymphocytes.

Polypeptides in accordance with the invention can comprise nonapeptides having an unbroken sequence of amino acids from SEQ. ID. NO. 1, or 2, wherein the amino acid adjacent to the N-terminal amino acid is L or M, preferably L, and the C-terminal amino acid is L, V or I, preferably L. Preferably, the amino acid in position 3 is Y, and/or the amino acid in position 4 is D, and/or the amino acid in position 5 is G, and/or the amino acid in position 7 is E, and/or the amino acid in position 8 is H. The amino acid positions are numbered from the N-terminal to the C-terminal, with the N-terminal amino acid in position 1. The polypeptides described above are preferably capable of complexing with a MHC molecule type HLA-A2, and preferably HLA-A2.1.

The invention, preferably, does not encompass nonapeptides having the amino acid sequences FLLFKYQMK (SEQ. ID. NO. 48), FIEGYCTPE (SEQ. ID. NO. 49), and GLELAQAPL (SEQ. ID. NO. 50).

The inventive polypeptide alternatively can be a decapeptide comprising a nonapeptide as defined above and, preferably, an unbroken sequence of amino acids from SEQ. ID. NO. 1, or 2. In preferred embodiments the nonapeptide has the amino acid sequence GLYDGMEHL (SEQ. ID. NO. 42) or GLYDGREHS (SEQ. ID. NO. 43), preferably GLYDGMEHL (SEQ. ID. NO. 42). In embodiments, the decapeptide can have the amino acid sequence GLYDGMEHLI (SEQ. ID. NO. 44) or GLYDGREHSV (SEQ. ID. NO. 45), preferably GLYDGMEHLI (SEQ. ID. NO. 44).

In a further aspect, the present invention comprises a polypeptide or protein of up to about 93 amino acids in length which comprises a nonapeptide or a decapeptide as defined above. Such a polypeptide or protein can comprise or consist of an unbroken sequence of amino acids from SEQ. ID. NO. 1, or 2, preferably SEQ. ID. NO. 1.

It is preferred that polypeptides in accordance with the present invention are capable of eliciting an immune response from human lymphocytes, preferably when complexed with an MHC molecule type HLA-A2, preferably HLA-A2.1. The immune response is preferably a cytolytic response from human T-lymphocytes, preferably CD8 T-cells.

In a further aspect, the present invention provides a polypeptide or protein comprising a polypeptide as defined above, wherein the amino acid sequence of said polypeptide or protein is not either of the complete sequences set out in SEQ. ID. NOs. 1 and 2, or that coded for by nucleotides 334-918 of SEQ. ID. NO. 7 (FIG. 13).

The invention also extends to polypeptides or proteins which are functionally equivalent homologues to any of the above defined polypeptides or proteins, but with the proviso that the amino acid sequence of said polypeptide or protein is not an entire sequence as set out in either of SEQ. ID. NOs. 1 and 2, or that coded for by nucleotides 334-918 of SEQ. ID. No. 7. In embodiments of the invention, the polypeptides can be complexed with an MHC molecule type HLA-A2, preferably HLA-A2.1.

In another aspect, the present invention provides nucleic acid molecules, each comprising a nucleotide sequence coding for a polypeptide or protein in accordance with previously defined aspects of the invention or a complimentary nucleotide sequence, wherein said nucleotide sequence is not an entire sequence as set out in any of SEQ. ID. NO. 3 (FIG. 9), SEQ. ID. NO. 4 (FIGS. 10a and 10b), SEQ. ID. NO. 5 (FIGS. 11a and 11b), SEQ. ID. NO. 6 (FIG. 12) and SEQ. ID. NO. 7 (FIG. 13). Such a nucleic acid molecule can comprise an unbroken sequence of nucleotides from SEQ. ID. NO. 3, 4 or 5, or a complimentary sequence, or an RNA transcript of said nucleic acid molecule.

In a preferred embodiment, such a nucleic acid molecule can encode a plurality of epitopes or a polytope.

In a further aspect, the present invention provides expression vectors, each comprising a nucleic acid molecule as previously defined, operably linked to a promoter. Expression vectors in accordance with the invention can comprise a nucleotide sequence coding for an MHC molecule type HLA-A2, preferably HLA-A2.1, a cytokine or a co-stimulatory molecule, or a bacterial or viral genome or a portion thereof.

In an additional aspect, the present invention relates to host cells, each transformed or transfected with an expression vector in accordance with the invention. Such a host cell can be transformed or transfected with an expression vector coding for an MHC molecule type HLA-A2, preferably HLA-A2.1, and/or a cytokine or a co-stimulatory molecule.

In a yet further aspect, the present invention provides polypeptide-binding agents, each of which can selectively bind or is specific for an isolated polypeptide or protein in accordance with the invention. A polypeptide-binding agent in accordance with the invention can comprise an antibody, preferably a monoclonal antibody or an antibody fragment specific for an isolated polypeptide in accordance with the invention. Preferably, such polypeptide-binding agents can selectively bind or are specific for a complex of a polypeptide in accordance with the invention and an MHC molecule type HLA-A2, preferably HLA-A2.1, but do not bind said major histocompatibility molecule alone. Further polypeptide-binding agents in accordance with the invention include CTLs and CTL clones which recognise and selectively lyse cells which carry a polypeptide in accordance with the invention complexed with an MHC molecule type HLA-A2, preferably HLA-A2.1.

In another aspect, the present invention relates to the use of a polypeptide or protein, isolated nucleic acid molecule, expression vector, host cell, or polypeptide-binding agent in accordance with the invention, in the therapy, prophylaxis, or diagnosis of disease and, preferably, of tumours. Thus, the invention also relates to pharmaceutical compositions for the prophylaxis, therapy or diagnosis of disease, preferably of tumours, comprising a polypeptide or protein, a nucleic acid molecule, an expression vector, a host cell, or a polypeptide-binding agent in accordance with the invention, optionally in admixture with a pharmaceutically acceptable carrier and optionally further comprising a major histocompatibility molecule type HLA-A2, preferably HLA-A2.1. Such pharmaceutical compositions can be employed as anti-tumour vaccines. Optionally pharmaceutical compositions in accordance with the invention can include other TRAs or TRAPs, expression vectors or host cells expressing other TRAs or TRAPs, or polypeptide-binding agents specific for other TRAs or TRAPs. In another embodiment, pharmaceutical compositions in accordance with the invention can further comprise a co-stimulatory molecule.

In a preferred embodiment, a pharmaceutical composition in accordance with the invention comprises an antigen presenting cell (APC), preferably a dendritic cell, which has been pulsed with a polypeptide in accordance with the invention so as to present on its surface said peptide as a complex with a major histocompatibility molecule, HLA.

In another aspect, the present invention provides peptide-pulsed antigen presenting cells.

In a yet further aspect, the invention relates to a method of diagnosing disease, preferably cancer, comprising contacting a biological sample isolated from a subject with an agent that is specific for a polypeptide or protein in accordance with the invention, or a nucleic acid molecule in accordance with the invention and assaying for interaction between the agent and any of the polypeptide, protein or nucleic acid molecule in the sample as a determination of the disease. The polypeptide-binding agent employed in this aspect of the invention can be a polypeptide-binding agent in accordance with a previously described aspect of the invention.

The invention also relates to methods of producing cytolytic T-cell cultures reactive against tumour cells. Such a method can comprise steps of removing a lymphocyte sample from an individual and then culturing the lymphocyte sample with a polypeptide or protein in accordance with the invention, an expression vector in accordance with the invention, or a host cell in accordance with the invention. Products comprising cytolytic T-cells reactive against a tumour cell expressing an antigen comprising a polypeptide or protein in accordance with the invention, can be used in the prophylaxis, therapy or diagnosis of disease preferably of tumours, are also encompassed in the present invention, particularly when obtained or obtainable by the aforementioned method.

BRIEF DESCRIPTION OF THE FIGURES

FIG. 3. Shows the identification of the region coding for the antigenic peptide recognised by CTL 447A/5. PCR fragments of different lengths as indicated were cloned into pcDNAI/Amp and cotransfected into COS-7 cells with gene HLA-A2.1. Transfected cells were incubated for 24 h with CTL 447A/5 and the TNF in the supernatants was measured by its toxicity to WEHI-164.13 cells.

FIG. 7. Shows the amino acid sequence of the protein encoded by the MAGE-A10 gene (SEQ. ID. NO. 1).

FIG. 8. Shows the amino acid sequence of the protein encoded for by the MAGE-A8 gene (SEQ. ID. NO. 2).

FIG. 9. Shows the nucleotide sequence of the MAGE-A10 gene (SEQ. ID. NO. 3).

FIGS. 10a and 10b. Show the nucleic acid sequence of MAGE-A10 cDNA, the region coding for the amino acid sequence in SEQ. ID. NO. 1 lying between bases 357 and 1466 (SEQ. ID. NO. 4).

FIGS. 11a and 11b. Show the nucleotide sequence of the MAGE-A8 gene (SEQ. ID. NO. 5).

FIG. 12. Shows a partial sequence of the MAGE-A8 gene as published in WO92/20356, with the codons in the coding portion of the gene identified (SEQ. ID. No. 6).

FIG. 13. Shows a partial sequence of the MAGE-A10 gene as published in WO92/20356, with the codons in the coding portion of the sequence identified (SEQ. ID. NO. 7).

BRIEF DESCRIPTION OF THE SEQUENCES

Figure 1:
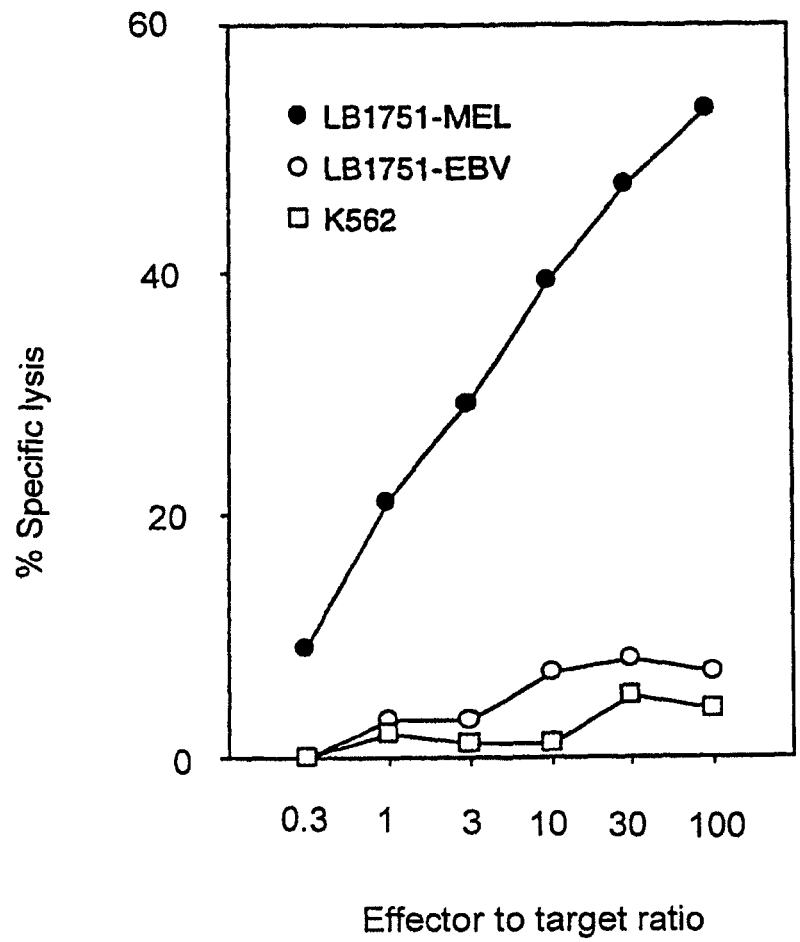
FIG. 1. Shows the specific lysis of autologous LB 1751-MEL cells by CTL 447A/5. Control targets included autologous EBV-transformed lymphoblastoid line LB1751-EBV and NK-sensitive line K562. Chromium release was measured after 4 h of incubation of chromium labelled target cells with the CTL at different effector to target ratios.

SEQ. ID. NO. 1 is the amino acid sequence of the protein encoded by the MAGE-A10 gene;

SEQ. ID. NO. 2 is the amino acid sequence of the protein encoded for by the MAGE-A8 gene;

SEQ. ID. NO. 3 is the nucleotide sequence of the MAGE-A10 gene;

SEQ. ID. NO. 4 is the nucleic acid sequence of MAGE-A10 cDNA, the region coding for the amino acid sequence in SEQ. ID. NO. 1 lies between bases 357 and 1466;

SEQ. ID. NO. 5 is the nucleotide sequence of the MAGE-A8 gene;

SEQ. ID. No. 6 is a partial sequence of the MAGE-A8 gene as published in WO92/20356, with the codons in the coding portion of the gene identified; and SEQ. ID. NO. 7 is a partial sequence of the MAGE-A10 gene as published in WO92/20356, with the codons in the coding portion of the sequence identified;

SEQ. ID. NOs. 8-41 are described in Table A;

SEQ. ID. NO. 42 is the nonapeptide with the amino acid sequence GLYDGMEHL;

SEQ. ID. NO. 43 is the nonapeptide with the amino acid sequence GLYDGREHS;

SEQ. ID. NO. 44 is the decapeptide with the amino acid sequence GLYDGMEHLI;

SEQ. ID. NO. 45 is the decapeptide with the amino acid sequence GLYDGREHSV;

SEQ. ID. NO. 46 is the nonapeptide with the amino acid sequence MLLVFGIDV;

SEQ. ID. NO. 47 is the decapeptide with the amino acid sequence CMLLVFGIDV;

SEQ. ID. NO. 48 is the nonapeptide with the amino acid sequence FLLFKYQMK;

SEQ. ID. NO. 49 is the nonapeptide with the amino acid sequence FIEGYCTPE;

SEQ. ID. NO. 50 is the nonapeptide with the amino acid sequence GLELAQAPL;

SEQ. ID. NO. 51 is the sense primer referred to in Example 3;

SEQ. ID. NO. 52 is the first anti-sense primer referred to in Example 3;

SEQ. ID. NO. 53 is the second anti-sense primer referred to in Example 3;

SEQ. ID. NO. 54 is the third anti-sense primer referred to in Example 3;

SEQ. ID. NO. 55 is the sense primer referred to in Example 6; and

SEQ. ID. NO. 56 is the anti-sense primer referred to in Example 6.

DETAILED DESCRIPTION OF THE INVENTION

As set out above, the present invention can involve the use of expression vectors to transform or transfect host cells and cell lines. Thus, a coding DNA sequence in accordance with the invention can be introduced into an expression vector suitable for directing expression of a polypeptide or protein in accordance with the invention (coded for by that DNA sequence) in a host cell. Suitable vectors include bacterial plasmids, phage DNA, cosmids, yeast plasmids and viral DNA, such as pox virus (e.g. vaccinia), retrovirus, baculovirus and adenovirus DNA. The procedure generally involves inserting a DNA sequence to be expressed into an appropriate restriction endonuclease site so that it is operably linked to a promoter for directing mRNA synthesis. A coding sequence and regulatory sequence, such as a promoter sequence, are considered to be "operably" linked when they are covalently linked in such a way as to place the expression or transcription of the coding sequence under the influence or control of the regulatory sequence. The resulting vector may then be employed to transform or transfect an appropriate host cell to cause that host cell to express the required polypeptide or protein. Appropriate host cells can be higher eukaryotic cells, such as mammalian cells and insect cells or can be lower eukaryotic cells, such as yeast cells, or prokaryotic cells, such as bacterial cells. Examples include E-coli, Bowes melanoma, CHO and COS cells. Selection of an appropriate host and the manner in which the vector is introduced into the host cell are matters within the knowledge of those skilled in the art. However appropriate techniques, cloning and expression vectors for use with prokaryotic and eukaryotic hosts are described in Sambrook et al, Molecular Cloning, A Laboratory Manual, Second edition, Coldspring Harbour, N.Y., 1989.

Expression vectors in accordance with the invention can include a nucleic acid sequence coding for the HLA molecule that presents a particular polypeptide in accordance with the invention. Alternatively, the nucleic acid sequence coding for the HLA molecule can be contained within a separate expression vector within a host cell in accordance with the invention. In a situation where the vector contains both coding sequences, the single vector can be used to transfect the cell which does not normally express either one. Where the coding sequence for the inventive polypeptide or protein and the HLA molecule which presents the former are contained on separate expression vectors, the expression vectors can be cotransfected. Sequences coding for polypeptides or proteins in accordance with the invention may be used alone, when, e.g. the host cell already expresses an HLA molecule which presents the TRA.

Preferred systems for mRNA expression in mammalian cells include the pRc/CMV (available from Invitrogen, Carlsbad, Calif., USA) system that contains a selectable marker such as a gene that confers G418 resistance (which facilitates the selection of stably transfected cell lines) and the human cytomegalovirus (CMV) enhancer-promoter sequences. Additionally, suitable for expression in primate or canine cells lines is the pCEP4 vector (Invitrogen), which contains an Epstein Barr virus (EBV) origin of replication, facilitating the maintenance of plasmid as a multicopy extrachromosomal element. Another expression vector is the pEF-BOS plasmid containing the promoter of polypeptide Elongation Factor 1α, which stimulates efficiently transcription in vitro. The plasmid is described by Mishizuma and Nagata (Nuc. Acids Res. 18:5322, 1990), and its use in transfection experiments is disclosed by, for example, Demoulin (Mol. Cell. Biol. 16:4710-4716, 1996). A further preferred expression vector is an adenovirus, described by Stratford-Perricaudet, which is defective for E1 and E3 proteins (J. Clin. Invest. 90:626-630, 1992). The use of the adenovirus as an adeno-P1A recombinant is disclosed by Warnier et al: in Intradermal injection in mice for immunisation against P1A (Int. J. Cancer, 67:303-310, 1996).

As stated above, the invention can involve polypeptide-binding agents specific for or selective for polypeptides or proteins in accordance with the invention. An agent should be considered as "specific" for a particular polypeptide or protein if it is capable of interacting with that polypeptide or protein in a manner which can be distinguished from its interaction with other molecules in the context in which it is used. For example, such an agent may be capable of selectively binding to a relevant polypeptide or protein under the conditions prevalent in a particular assay. The term "contacting" means that a biological sample is placed in sufficient proximity to an agent and under appropriate conditions of, for example, concentration, temperature, time, to allow the specific interaction between the agent and any polypeptide or protein for which it is specific, to take place. Appropriate conditions for contacting agents and biological samples are well known to those skilled in the art and are selected to facilitate the specific interaction between particular target molecules and specific agents. Polypeptide-binding agents can be used in this way in screening assays to detect the presence or absence of proteins or polypeptides in accordance with the invention and in purification protocols to isolate such proteins and polypeptides. Polypeptide-binding agents in accordance with the invention can be in the form of immobilised antibodies attached to a substrate and the inventive method of diagnosing disease can involve a conventional enzyme-linked immunosorbent assay (ELISA) carried out on a protein containing biological sample derived from a patient. Alternatively, the method can comprise a Western blot in which the agent is a labelled antibody and the biological sample comprises proteins derived from a patient and separated by electrophoresis on an SDS polyacrylamide gel. Polypeptide-binding agents can be used to selectively target drugs, toxins or other molecules to cancer cells which present polypeptides in accordance with the invention. In this manner, cells present in tumours which express polypeptides or proteins in accordance with the invention can be treated with cytotoxic compounds.

As stated, the invention can involve antibodies or fragment of antibodies having the ability to selectively bind to polypeptides or proteins in accordance with the invention. Such antibodies include polyclonal and monoclonal antibodies, prepared according to the conventional methodology.

The antibodies of the present invention can be prepared by any of a variety of methods, including administering protein, fragments of protein, cells expressing the protein or fragments thereof and the like to an animal to induce polyclonal antibodies. The production of monoclonal antibodies is according to techniques well known in the art. Such antibodies may be used for example to identify tissues expressing protein or to purify protein. Antibodies also may be coupled to specific labelling agents for imaging or to antitumour agents, including, but not limited to, methotrexate, radioiodinated compounds, toxins such as ricin, other cystostatic or cytolytic drugs, and so forth. Antibodies prepared according to the invention also preferably are specific for the TRA/HLA complexes described herein.

Significantly, as is well known in the art, only a small portion of an antibody molecule, the paratope, is involved in the binding of the antibody to its epitope (see, in general, Clark W. R. (1986) The Experimental Foundations of Modern Immunology Wiley & Sons, Inc., New York; Roitt, I. (1991) Essential Immunology, $7^{th}$ Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F(ab')$_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well known in the art, there are complementarity determining regions (CDRs), which directly interact with the epitope of the antigen, and framework regions (FRs), which maintain the tertiary structure of the paratope (see in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well established in the art that the non-CDR regions of a mammalian antibody may be replaced with similar regions of nonspecific or heterospecific antibodies while retaining the epitope specificity of the original antibody. This is most clearly manifested in the development and use of "humanised" antibodies which non-human CDRs are covalently joined to human FR and/or Fc/Fc' regions to produce a functional antibody. Thus, for example, PCT International Publication Number WO92/04381 teaches the production and use of humanised murine RSV antibodies in which at least a portion of the murine FR regions have been replaced by FR regions of human origin. Such antibodies, including fragments of intact antibodies with antigen-binding ability, are often referred to as "chimeric" antibodies.

Thus, as will be apparent to one of ordinary skill in the art, the present invention also provides for F(ab')$_2$, Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')$_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies. Thus, the invention can involve polypeptides of numerous sizes and types that bind specifically or selectively to polypeptides and proteins in accordance with the invention. These polypeptides may be derived also from sources other than antibody technology. For example, such polypeptide binding agents can be provided by degenerate peptide libraries which can be readily prepared in solution, in immobilised form or as phage display libraries. Combinatorial libraries can also be synthesized of peptides containing one or more amino acids. Libraries further can be synthesized of peptiods and non-peptide synthetic moieties.

Phage display can be particularly effective in identifying binding peptides useful according to the invention. Briefly, one prepares a phage library (using e.g. m13, fd, or lambda phage), displaying inserts from 4 to about 80 amino acid residues using conventional procedures. The inserts may represent a completely degenerate or biased array. One can then select phage-bearing inserts which bind to a polypeptide or protein in accordance with the invention. This process can be repeated through several cycles of reselection of phage that bind to a polypeptide or protein in accordance with the invention. Repeated rounds lead to enrichment of phage bearing particular sequences. DNA sequence analysis can be conducted to identify the sequences of the expressed polypeptides. The minimal linear portion of the sequence that binds to a polypeptide or protein in accordance with the invention can be determined. One can repeat the procedure using a biased library containing inserts containing part or all of the minimal linear portion plus one or more additional degenerate residues upstream or downstream thereof. Thus, a polypeptide or protein in accordance with the invention can be used to screen peptide libraries, including phage display libraries, to identify and select peptide binding partners of the polypeptides of the invention. Such molecules can be used, as described, for screening assays, for diagnostic assays, for purification protocols or for targeting drugs, toxins and/or labelling agents (e.g. radioisotopes, fluorescent molecules, etc.) to cells which express a polypeptide or protein in accordance with the invention on the cell surface. Such binding agent molecules can also be prepared to bind complexes of a polypeptide or protein in accordance with the invention and an HLA molecule by selecting the binding agent using such complexes. Drug molecules that would disable or destroy tumour cells which express such complexes are known to those skilled in the art and are commercially available. For example, the immunotoxin art provides examples of toxins which are effective when delivered to a cell by an antibody or fragment thereof. Examples of toxins include ribosome-damaging toxins derived from plant or bacterial such as ricin, abrin, saporin, Pseudomonas endotoxin, diphtheria toxin, A chain toxins, blocked ricin, etc.

The invention as described herein has a number of uses, some of which are described herein. First the invention permits the diagnosis of a disorder characterised by an expression of a polypeptide or protein in accordance with the invention. The methods can involve determining expression of the gene coding for a polypeptide or protein in accordance with the invention. In the former situation, such determinations can be carried out by any standard nucleic acid determination assay, including the polymerase chain reaction or assaying with labelled hybridisation probes, while in the latter situation, assaying with polypeptide-binding agents in accordance with the invention, such as antibodies, is preferred. An alternative method for determination is an assay for recognition of a TRA/HLA complex by a peptide-specific CTL by assaying for CTL activity. Such assays include a TNF release assay, of the type described below, a chromium release assay or a technique called ELISPOT in which CTL activity can be detected via antibody detection of IFN-γ or TNFα release (Schmittel et al (1997). J. Immunol. Methods 210:167-174 and Lalvani et al. J. Exp. Med. 186:859-865 (1997)).

Other TRAPs or TRAs recognised by the CTL clones described herein may be isolated by the procedures detailed herein.

A variety of methodologies well known to the skilled practitioner can be utilised to obtain isolated TRA and TRAP molecules such as those which are the subject of the present invention. The protein may be purified from cells which naturally produce the protein. Alternatively, an expression vector may be introduced into cells to cause production of the protein. In another method, mRNA transcripts may be microinjected or otherwise introduced into cells to cause the production of the encoded protein. Translation of mRNA in cell-free extracts such as reticulocyte lysate system also may be used to produce protein. Peptides comprising TRAs of the invention may also be synthesised in vitro. Those skilled in the art can also readily follow known methods for isolating proteins in order to obtain isolated TRAPs and/or TRAs derived therefrom. These include, but are not limited to, immunochromatography, HPLC, size-exclusion chromatography, ion-exchange chromatography and immune-affinity chromatography.

Polypeptides or proteins in accordance with the invention or complexes thereof with HLA, again in accordance with the invention, may be combined with materials such as adjuvants to produce vaccines useful in treating disorders characterised by expression of a polypeptide or protein in accordance with the invention.

Certain therapeutic approaches based upon the disclosure are premised on a response by the subject's immune system, leading to lysis of TRA presenting cells. One such approach is the administration of autologous CTLs specific to the complex to a subject with abnormal cells of the phenotype at issue. It is within the skill of the artisan to develop such CTLs in vitro. Generally, a sample of cells taken from a subject, such as blood cells, are contacted with a cell presenting the complex and capable of provoking CTLs to proliferate. The target cell can be a transfectant, such as a COS cell. These transfectants present the desired complex on their surface and, when combined with a CTL of interest, stimulate its proliferation. COS cells, such as those used herein are widely available, as are other suitable host cells. Specific production of a CTL is well known to one of ordinary skill in the art. One method for selecting antigen-specific CTL clones has recently been described (Altman et al., Science 274:94-96, 1996; Dunbar et al., Curr. Biol. 8:413-416, 1998), in which fluorogenic tetramers of MHC class I molecule/peptide complexes are used to detect specific CTL clones. Briefly, soluble MHC class I molecules are folded in vitro in the presence of $\beta_2$-microglobulin and a peptide antigen which binds the class I molecule. After purification, the MHC/peptide complex is purified and labelled with biotin. Tetramers are formed by mixing the biotinylated peptide-MHC complex with labelled avidin (e.g. phycoerythrin) at a molar ratio of 4:1. Tetramers are then contacted with a source of CTLs such as peripheral blood or lymph node. The tetramers bind CTLs which recognise the peptide antigen/MHC class I complex. Cells bound by the tetramers can be sorted by fluorescence activated cell sorting to isolate the reactive CTLs. The isolated CTLs then can be expanded in vitro. The clonally expanded autologous CTLs then can be administered to the subject. Other CTLs specific to a polypeptide or protein in accordance with the invention may be isolated and administered by similar methods.

To detail a therapeutic methodology, referred to as adoptive transfer (Greenberg. J. Immunol. 136(5):1917, 1986; Riddel et al. Science 257:238, 1992; Lynch et al, Eur. J. Immunol. 21:1403-1410, 1991; Kast et al., Cell 59:603-614, 1989), cells presenting the desired complex are combined with peripheral blood lymphocytes containing CTLs leading to proliferation of the CTLs specific thereto. The proliferated CTLs are then administered to a subject with a cellular abnormality which is characterised by certain of the abnormal cells presenting the particular complex. The CTLs then lyse the abnormal cells, thereby achieving the desired therapeutic goal.

The foregoing therapy assumes that at least some of the subject's abnormal cells present the relevant HLA/TRA complex. This can be determined very easily, as the art is very familiar with methods for identifying cells which present a particular HLA molecule, as well as how to identify cells expressing DNA or protein of the pertinent sequences. In this case, MAGE-A10 expression could be determined, for example, by conducting a PCR assay using primers from unique parts of the MAGE-A10 DNA. Alternatively, other well known antibody based techniques can be employed to identify cells presenting a relevant TRA/HLA complex. Once cells presenting the relevant complex are identified via the foregoing screening methodology, they can be combined with a sample from a patient containing CTLs. If the complex presenting cells are lysed by the mixed CTL sample, then it can be assumed that the TRA is being presented, and the subject is an appropriate candidate for the therapeutic approaches set forth herein.

Adoptive transfer is not the only form of therapy that is available in accordance with the invention. CTLs can also be provoked in vivo, using a number of approaches.

One approach is the use of non-proliferative cells expressing the complex as vaccines. Such vaccines can be prepared from cells, which can be host cells in accordance with the invention, that present TRA/HLA complexes on their surface. The cells used in this approach may be those that normally express the complex, such as irradiated non-proliferative tumour cells or non-proliferative transfectants etcetera. Chen et al., Proc. Natl. Acad. Sci. USA 88:110-114 (1991) exemplifies this approach, showing the use of transfected cells expressing HPV E7 peptides in a therapeutic regime. Various cell types may be used. Similarly, vectors carrying one or both of the genes of interest may be used. Viral or bacterial vectors are especially preferred. For example, nucleic acids which encode a polypeptide or protein in accordance with the invention may be operably linked to promoter and enhancer sequences which direct expression of the polypeptide or protein in accordance with the invention in certain tissues or cell types. The nucleic acid may be incorporated into an expression vector. Expression vectors may be unmodified extrachromosomal nucleic acids, plasmids or viral genomes constructed or modified to enable insertion of exogenous nucleic acids, such as those encoding a polypeptide or protein in accordance with the invention. Nucleic acids encoding a polypeptide or protein in accordance with the invention also may be inserted intro a retroviral genome, thereby facilitating integration of the nucleic acid into the genome of the target tissue or cell type. In these systems, the gene of interest is carried by a microorganism, e.g., a vaccinia virus, retrovirus or the bacteria BCG, and the materials de facto "infect" host cells. The cells which result present the complex of interest, and are recognised by autologous CTLs, which then proliferate. In all cases where cells are used as a vaccine, these can be cells transfected with coding sequences for one or both of the components necessary to provoke a CTL response, or be cells which already express both molecules without the need for transfection. These cells can also be antigen presenting cells (APCs), such as dendritic cells (DC) which have been "pulsed" with the TRAs of the invention or peptides derived therefrom (Nestle et al. Nat. Med. 4:328-332, 1998; Mukherji et al. Proc. Nat. Acad. Sci. USA. 92:8078-8082, 1995; Hu et al. Cancer Res. 56:2479-2483, 1996).

Vaccines also encompass naked DNA or RNA, encoding a polypeptide or protein in accordance with the invention, which may be produced in vitro and administered via injection, particle bombardment, nasal aspiration and other methods. Vaccines of the "naked nucleic acid" type have been demonstrated to provoke an immunological response including generation of CTLs specific for the peptide encoded by the naked nucleic acid (Science 259:1745-1748, 1993). When "disorder" is used herein, it refers to any pathological condition where the tumour rejection antigen precursor is expressed. An example of such a disorder is cancer, particularly melanoma.

A similar effect can be achieved by combining a polypeptide or protein in accordance with the invention with an adjuvant to facilitate incorporation into HLA presenting cells in vivo. The polypeptide or protein in accordance with the invention complexes with a molecule which presents the polypeptide or protein in accordance with the invention without the need for further processing. Generally, subjects can receive an intradermal injection of an effective amount of a polypeptide or protein in accordance with the invention. Initial doses can be followed by booster doses, following immunisation protocols standard in the art.

Especially preferred are nucleic acids encoding a series of epitopes, known as "polytopes". The epitopes can be arranged in sequential or overlapping fashion (see, e.g. Thompson et al, Proc. Natl. Acad. Sci. USA 92:5845-5849, 1995; Gilbert et al, Nature Biotechnol. 15:1280-1284, 1997) with or without the natural flanking sequences, and can be separated by unrelated linker sequences if desired. The polytope is processed to generated individual epitopes which are recognized by the immune system for generation of immune responses.

Thus, for example, peptides in accordance with the invention and which are presented by MHC molecules and recognised by CTL or T helper lymphocytes can be combined with peptides from other tumour rejection antigens (e.g. by preparation of hybrid nucleic acids or polypeptides) to form "polytopes". Exemplary tumour associated peptide antigens that can be administered to induce or enhance an immune response are derived from tumour associated genes and encoded proteins including MAGE-1, MAGE-2, MAGE-3, MAGE-4, MAGE-5, MAGE-6, MAGE-7, MAGE-8, MAGE-9, MAGE-10, MAGE-11, MAGE-12, MAGE-13, GAGE-1, GAGE-2, GAGE-3, GAGE-4, GAGE-5, GAGE-6, GAGE-7, GAGE-8, BAGE-1, RAGE-1, RAGE-2, RAGE-3, RAGE-4, LB33/MUM-1, DAGE (PRAME), NAG, MAGE-Xp2 (MAGE-B2), MAGE-Xp3, (MAGE-B3), MAGE-Xp4 (MAGE-B4), tyrosinase, brain glycogen phosphorylase, Melan-A, MAGE-C1, MAGE-C2, NY-ESO-1, LAGE-1, SSX-1, SSX-2 (HOM-MEL-40), SSX-4, SSX-5, SCP-1 and CT-7. for example, antigenic peptides characteristic of tumour include those listed in Table A below.

TABLE A

Exemplary Antigens

| Gene | MHC | Peptide | Position | SEQ ID NO: |
|---|---|---|---|---|
| MAGE-1 | HLA-A1 | EADPTGHSY | 161-169 | 8 |
|  | HLA-Cw16 | SAYGEPRKL | 230-238 | 9 |
| MAGE-3 | HLA-A1 | EVDPIGHLY | 168-176 | 10 |
|  | HLA-A2 | FLWGPRALV | 271-279 | 11 |
|  | HLA-B44 | MEVDPJGHLY | 167-176 | 12 |
| BAGE | HLA-Cw16 | AARAVFLAL | 2-10 | 13 |
| GAGE-1, 2 | HLA-Cw16 | YRPRPRRY | 9-16 | 14 |
| RAGE | HLA-B7 | SPSSNRIRNT | 11-20 | 15 |
| GnT-V | HLA-A2 | VLPDVFIRC(V) | 2-10/11 | 16, 17 |
| MUM-1 | HLA-B44 | EEKLIVVLF | exon 2/intron | 18 |
|  |  | EEKLSVVLF (wild type) |  | 19 |
| CDK4 | HLA-A2 | ACDPHSGHFV | 23-32 | 20 |
|  |  | ARDPHSGHFV (wild type) |  | 21 |
| β-catenin | HLA-A24 | SYLDSGIHF | 29-37 | 22 |
|  |  | SYLDSGIHS (wild type) |  | 23 |

TABLE A-continued

Exemplary Antigens

| | | | | |
|---|---|---|---|---|
| Tyrosinase | HLA-A2 | MLLAVLYCL | 1-9 | 24 |
| | HLA-A2 | YMNGTMSQV | 369-377 | 25 |
| | HLA-A2 | YMDGTMSQV | 369-377 | 41 |
| | HLA-A24 | AFLPWHRLF | 206-214 | 26 |
| | HLA-B44 | SEIWRDIDF | 192-200 | 27 |
| | HLA-B44 | YEIWRDIDF | 192-200 | 28 |
| | HLA-DR4 | QNILLSNAPLGPQFP | 56-70 | 29 |
| | HLA-DR4 | DYSYLQDSDPDSFQD | 448-462 | 30 |
| MELAN-A$^{MART-1}$ | HLA-A2 | (E)AAGIGILTV | 26/27-35 | 31, 32 |
| | HLA-A2 | ILTVILGVL | 32-40 | 33 |
| gp100$^{Pmel117}$ | HLA-A2 | KTWGQYWQV | 154-162 | 34 |
| | HLA-A2 | ITDQVPFSV | 209-217 | 35 |
| | HLA-A2 | YLEPGPVTA | 280-288 | 36 |
| | HLA-A2 | LLDGTATLRL | 457-466 | 37 |
| | HLA-A2 | VLYRYGSFSV | 476-485 | 38 |
| DAGE (PRAME) | HLA-A24 | LYVDSLFFL | 301-309 | 39 |
| MAGE-6 | HLA-Cw16 | KISGGPRISYPL | 292-303 | 40 |

Other examples will be known to one of ordinary skill in the art (for example, see Coulie, Stem Cells 13:393-403, 1995) and can be used in the invention in a like manner as those disclosed herein. One of ordinary skill in the art can prepare polypeptides comprising one or more MAGE-A10 peptides and one or more of the foregoing tumour rejection peptides, or nucleic acids encoding such polypeptides, according to standard procedures of molecular biology.

Thus polytopes are groups of two or more potentially immunogenic or immune response stimulating peptides which can be joined together in various arrangements (e.g. concatenated, overlapping). The polytope (or nucleic acid encoding the polytope) can be administered in a standard immunization protocol, e.g. to animals, to test the effectiveness of the polytope in stimulating, enhancing and/or provoking an immune response.

The polypeptides can be joined together to directly or via the use of flanking sequences to form polytopes, and the use of polytopes as vaccines is well known in the art (see e.g., Thomson et al. Proc. Acad. Sci. USA 92(13):5485-5849), 1995; Gilbert et al, Nature Biotechnol. 15(12):1280:1284, 1997; Thomson et al., J. Immunol. 157(2):822:826, 1996; Tam et al., J. Exp. Med. 171(1):299-306, 1990). For example, Tam showed that polytopes consisting of both MHC class I and class II binding epitopes successfully generated antibody and protective immunity in a mouse model. Tam also demonstrated that polytopes comprising "strings" of epitopes are processed to yield individual epitopes which are presented by MHC molecules and recognised by CTLs. Thus polytopes containing various numbers and combinations of epitopes can be prepared and tested for recognition by CTLs and for efficacy in increasing an immune response.

It is known that tumours express a set of tumour antigens, of which only certain subsets may be expressed in the tumour of any given patient. Polytopes can be prepared which correspond to the different combination of epitopes representing the subset of tumour rejection antigens expressed in a particular patient. Polytopes can be prepared to reflect a broader spectrum of tumour rejection antigens known to be expressed by a tumour type. Polytopes can be introduced to a patient in need of such treatment as polypeptide structures, or via the use of nucleic acid delivery systems known in the art (see. e.g., Allsop et al., Eur. J. Immunol. 26(8):1951-1959, 1996). Adenovirus, pox virus, Ty-virus like particles, adeno-associated virus, plasmids, bacteria, etc. can be used in such a delivery. One can test the polytope delivery systems in mouse models to determine efficacy of the delivery system. The systems can also be tested in human clinical trials.

As part of the immunisation protocols, substances which potentiate the immune response may be administered with the nucleic acid or peptide components of a pharmaceutical composition or a cancer vaccine in accordance with the invention. Such immune response potentiating compound may be classified as either adjuvants or cytokines. Adjuvants may enhance the immunological response by providing a reservoir of antigen (extracellularly or within macrophages), activating macrophages and stimulating specific sets of lymphocytes. Adjuvants of many kinds are well known in the art; specific examples include MPL (SmithKline Beecham), a congener obtained after purification and acid hydrolysis of *Salmonella minnesota* Re 595 lipopolysaccharide. QS21 (SmithKline Beecham), a pure QA-21 saponin purified from *Quillja saponaria* extract, and various water-in-oil emulsions prepared from biodegradable oils such as squalene and/or tocopherol. Cytokines are also useful in vaccination protocols as a result of lymphocyte stimulatory properties. Many cytokines useful for such purposes will be known to one of ordinary skill in the art, including interleukin-12 (IL-12) which have been shown to enhance the protective effects of vaccines (Science 268:1432-1434, 1995), GM-CSF and IL-18. As envisaged herein, cytokines can be produced in vivo by cells transformed or transfected to express nucleic acid molecules coding therefor.

There are a number of additional immune response potentiating compounds that can be used in vaccination protocols. These include co-stimulatory molecules provided in either protein or nucleic acid form. Such co-stimulatory molecules include the B7-1 and B7-2 (CD80 and CD86 respectively) molecules which are expressed on dendritic cells (DC) and interact with the CD28 molecule expressed on the T cell. This interaction provides costimulation (signal 2) to an antigen/MHC/TCR stimulated (signal 1) T cell, increasing cell proliferation and effector function. B7 also interacts with CTLA4 (CD152) on T cells and studies involving CTLA4 and B7 ligands indicate that the B7-CTLA4 interaction can enhance antitumour immunity and CTL proliferation (Zheng et al., Proc. Nat'l Acad. Sci. USA 95:6284-6289, 1998).

B7 typically is not expressed on tumour cells so they are not efficient antigen presenting cells (APCs) for T cells. Induction of B7 expression would enable the tumour cells to stimulate more efficiently CTL proliferation and effector function. A combination of B7/IL-6/IL-12 costimulation has been shown to induce IFN-gamma and a Th1 cytokine profile in the T cell population leading to further enhanced T cell activity (Gajewski et al., J. Immunol. 154:5637-5648, 1995). Tumour cell transfection with B7 has been discussed in relation to in vitro CTL expansion for adoptive transfer immunotherapy by Wang et al., (J. Immunol. 19:1-8, 1986). Other delivery mechanisms for the B7 molecule would include nucleic acid (naked DNA) immunization (Kim et al., Nature Biotechnol. 15:7:641-646, 1997) and recombinant viruses such as adeno and pox (Wendtner et al., Gene Ther. 4:726-735, 1997). These systems are all amenable to the construction and use of expression cassettes for the coexpression of B7 with other molecules of choice, such as polypeptides or proteins in accordance with the invention (including polytopes), or cytokines. These delivery systems can be used for induction of the appropriate molecules in vitro vaccination situations. The use of anti-CD28 antibodies to directly stimulate T cells in vitro and in vivo could also be considered.

Lymphocyte function associated antigen-3 (LFA-3) is expressed on APCs and some tumour cells and interacts with CD2 expressed on T cells. This interaction induces T cell IL-2 and IFN-gamma production and can thus complement but not substitute, the B7/CD28 co-stimulatory interaction (Parra et al., J. Immunol., 158:637-642, 1997; Fenton et al., J. Immunother. 21:95-108, 1998).

Lymphocyte function associated antigen-1 (LFA-1) is expressed on leukocytes and interacts with ICAM-1 expressed on APCs and some tumour cells. This interaction induces T cell IL-2 and IFN-gamma production and can thus complement but not substitute, the B7/CD28 co-stimulatory interaction (Fenton et al., 1998). LFA-1 is thus a further example of a co-stimulatory molecule that could be provided in a vaccination protocol in the various ways discussed above for B7.

Complete CTL activation and effector function requires Th cell help through the interaction between the Th cell CD40L (CD40 ligand) molecule and the CD40 molecule expressed by DCs (Ridge et al., Nature 393:474, 1998; Bennett et al., Nature 393:478, 1998; Schoenberger et al., Nature 393:480, 1998). This mechanism of this co-stimulatory signal is likely to involve upregulation of B7 and associated IL-6/IL-12 production by the DC (APC). The CD40-CD40L interaction thus complements the signal 1 (antigen/MHC-TCR) and signal 2 (B7-CD28) interactions.

The use of anti-CD40 antibodies to stimulate DC cells directly, would be expected to enhance a response to tumour associated antigens which are normally encountered outside of an inflammatory context or are presented by non-professional APCs (tumour cells). In these situations Th help and B7 costimulation signals are not provided. This mechanism might be used in the context of antigen pulsed DC based therapies or in situations where Th epitopes have not been defined within known tumour associated antigen precursors.

Pharmaceutical compositions in accordance with the present invention can be formulated with conventional pharmaceutically acceptable carriers and excipients, either for systemic or local administration. Such carriers and excipients can be selected without difficulty by those skilled in the art and include those which provide for immediate and sustained release.

Figure 6:
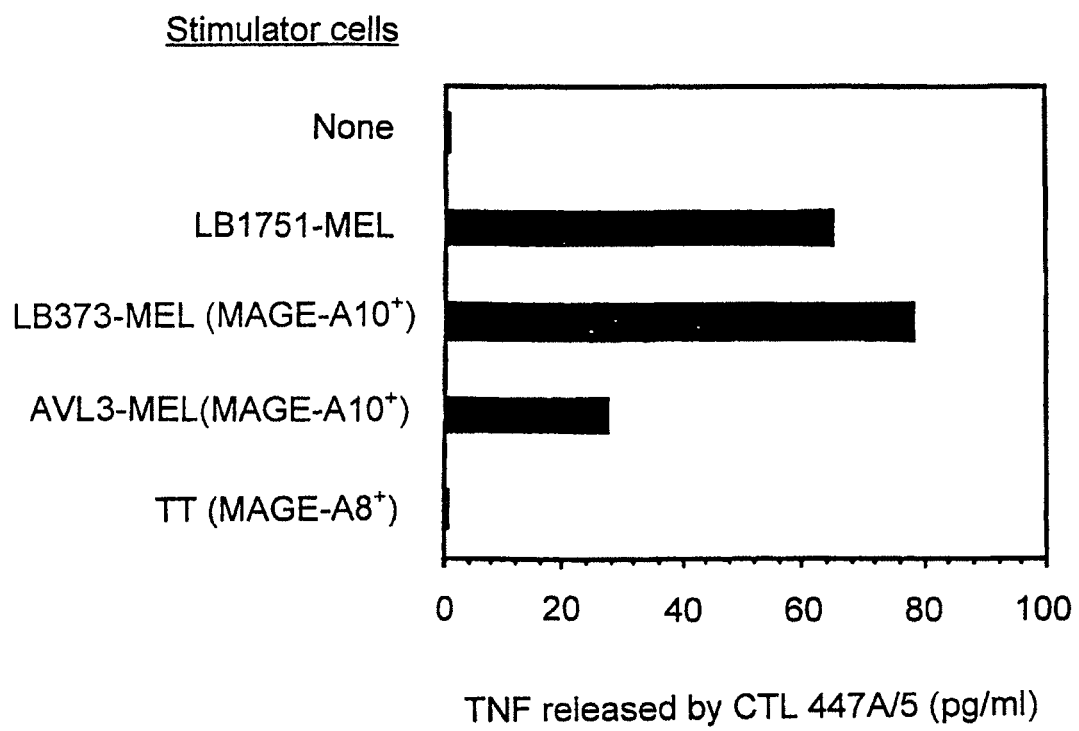
FIG. 6. Shows the degree of recognition of allogenic tumour cell lines by CTL 447A/5. LB373-MEL (MAGE-A10+), AVL3-MEL (MAGE-A10−) and TT (MAGE-A8−) cell lines derived from HLA-A2 patients were used to stimulate CTL 447A/5. Autologous tumour cell line LB1751-MEL was included as a control. After 24 h of coculture, production of TNF by the CTL was measured by testing toxicity of the supernatants to TNF-sensitive WEHI-164.13 cells.

The present invention involves the generation of MAGE-specific CTLs from a patient other than MZ2 by MLTC for the first time. A CTL clone (CTL 477A/5) was generated that recognises the nonapeptide (TRA) GLYDGMEHL (SEQ. ID. NO. 42) encoded by MAGE-A10 in the context of HLA-A2. Its overlapping decapeptide (TRA) GLYDGMEHLI (SEQ. ID. NO. 44) could also sensitise target cells to be lysed by the CTL, but less efficiently. CTL 447A/5 recognised not only autologous tumour cells but MAGE-A10+ tumour cells from other HLA-A2 patients (FIG. 6), suggesting that GLYDGMEHL (SEQ. ID. NO. 42) is a common TRA presented in tumours expressing MAGE-A10 and HLA-A2. MAGE-A10 is expressed in tumours more frequently than previously anticipated. By reverse-transcription-PCR, the expression of MAGE-A10 gene has been detected in a variety of tumours, including melanomas, lung cancers, head and neck carcinomas, bladder carcinomas, myelomas, prostatic carcinomas, and (see table 2 below). As observed for other MAGE genes, the only normal tissue expressing MAGE-A10 is testis.

Clinical trials have also been under way to treat melanoma patients with peptides derived from MAGE-A1 and MAGE-A3. A few patients showed objective tumour regressions after being immunised with pure peptides, though peptide-specific CTL responses were not detected (Marchand, M., et al., 1995, Int. J. Cancer. 63:883-885). When immunised with peptide-pulsed antigen presenting cells or dendritic cells, quite a few patients developed peptide-specific delayed-type hypersensitivity or CTL responses (Nestle, F. O., et al., 1998, Nat. Med. 4:328-332; Mukherji, B., N et al., 1995, Proc. Natl. Acad. Sci. USA. 92:8078-8082; and Hu, X., et al., 1996, Cancer Res. 56:2479-2483). One of the obstacles in cancer immunotherapy is the occurrence of antigen loss tumour variants. Since most tumours expressing MAGE-A10 also express MAGE-A1 or/and MAGE-A3 (F. Brasseur, unpublished data), it is anticipated that addition of peptides in accordance with the present invention in a cocktail vaccination will improve the anti-tumour effect by targeting several different antigens.

The following examples show the generation of cytolytic T lymphocytes (CTLs) from patent LB 1751, using MLTC techniques, that lysed specifically autologous tumour cells and produced tumour necrosis factor (TNF) upon stimulation with target cells expressing MAGE-A10. The recognition by the CTLs was shown to be restricted by HLA-A2.1 and the antigen was found to be encoded by MAGE-A10 in the region of nt 547-825. From the amino acid sequence corresponding to this region, four peptides were found that had the potential to bind to HLA-A2.1. The expression of MAGE-A10 has been detected in a variety of tumours, but not in normal tissues except testis and the identified antigenic peptides, therefore, clearly add to the repertoire of antigens that have the potential to be used in anti-tumoural vaccination trials.

EXAMPLES

Example 1

Preparation of CTL Clones Against LBI 751-MEL and Identification HLA-A2.1 as on the Presenting MHC Molecule Melanoma cell line LB1751-MEL was derived from a metastatic melanoma in axillary lymph nodes of a 67-yr-old male patient LB1751 and grown by a method previously described (Van den Eynde, B., et al., 1989, Int. J. Cancer. 44:634-640).

At passage 4 after the initiation of LB1751-MEL culture, aggregates of typical EBV-transformed lymphoblastoid cells appeared in the supernatant. They were collected and cultured separately to obtain B cell line LB 1751-EBV. Melanoma culture LB1751-MEL was cleared of EBV-transformed B cells by limiting dilution cloning.

DNA fingerprint confirmed that LB 1751-MEL and LB 1751-EBV originated from the same patient (data not shown). A panel of CTL clones was generated by MLTC as described previously with minor modifications (Herin, M., et al., 1987, Int. J. Cancer. 39:390-396). Briefly, MLTC was carried out by culturing PBL of patient LB1751 with irradiated LB1751-MEL cells in an 8% $CO_2$ incubator in Iscove's modified Dulbecco's medium (GIBCO BRL, Gaithersburg, Md.) supplemented with 10 mM Hepes buffer, L-arginine (116 μg/ml), L-asparagine (36 μg/ml), L-glutamine (216 g/ml), 10% human serum, and 5 ng/ml of recombinant human IL-7 (rhIL-7) (Genzyme, Cambridge, Mass.). On day 3, rhIL-2 (Eurocetus, Amsterdam, Netherlands) was added at a final concentration of 25 U/ml. Lymphocytes were restimulated weekly with irradiated LB1751-MEL cells in fresh medium containing 25 U/ml of rhIL-2 and 5 ngl/ml of rhIL-7. On day 21, CD8+ T lymphocytes were sorted by using anti-CD8-conjugated MACS magnetic MicroBeads (MACS, Miltenyi Biotec GmbH, Germany) and cloned by limiting dilution. The resulting panel of CTL clones specifically lysed LB1751-MEL cells, but not autologous EBV-transformed B cell line LB 1751-EBV or NK-sensitive cell line K562. Lysis of target cells was tested by chromium release as previously described in (Boon, T., et al., 1980, J. Exp. Med. 152:1184-1193) and the results of these tests for representative CTL clone 447A/5 are shown in FIG. 1.

Figure 2:
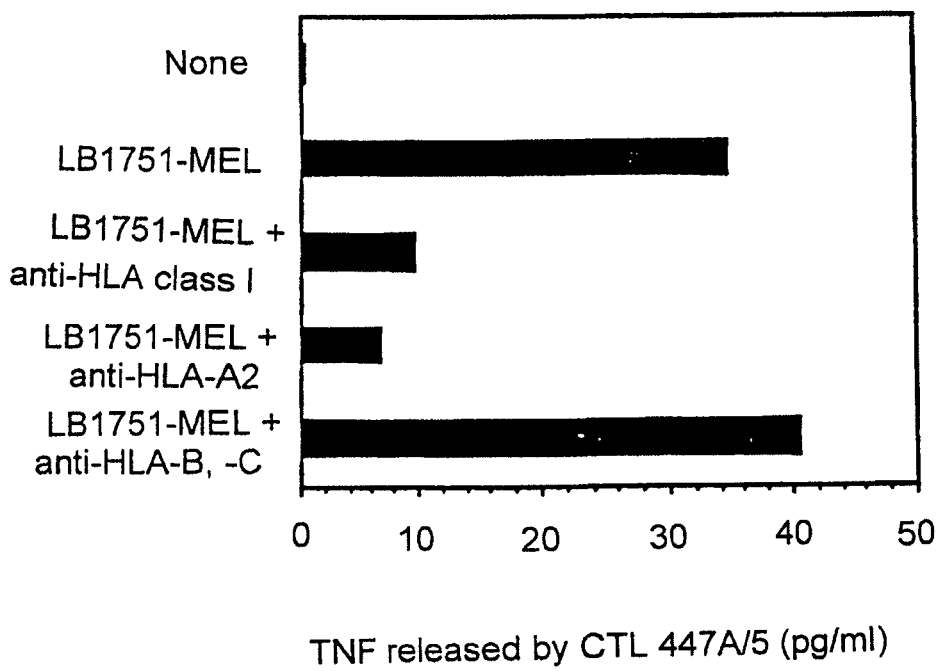
FIG. 2. Shows the HLA-restricted recognition of LB1751-MEL cells by CTL 447A/5. LB1751-MEL cells alone or in the presence of mAbs with the specificities indicated were used to stimulate CTL 447A/5. After 24 h of coculture, production of TNF by the CTL was measured by testing toxicity of the supernatants to TNF-sensitive WEHI-164.13 cells.

The ability of CTL clone 447A/5 to produce TNF when stimulated with LB1751-MEL cells was confirmed using the technique described in (Traversari, C., et al., 1992, Immunogenetics. 35:145-152). Briefly, $2 \times 10^4$ tumour cells were grown for 24 h. The medium was discarded and 3,000 CTL were added to the microwells in 100 μl of Iscove's modified Dulbecco's medium supplemented with 10% human serum and 25 U/ml rhIL-2. After 24 h, the supernatant was collected and its TNF content was determined by testing its cytotoxic effect on WEHI 164 clone 13 cells (Espevik, T., et al., 1986, J. Immunol. Methods. 95:99-105) in a MTT colorimetric assay (Traversari, C., et al., 1992, Immunogenetics. 35:145-152; and Hansen, M. B., et al., 1989, J. Immunol. Methods. 119:203-210). Inhibition of TNF production by mAbs W6/32 (anti-HLA class 1) (Bamstable, C. J., et al., 1978, Cell. 14:9-20), BB7.2 (anti-HLA-A2) (Parham, P., and F. M. Brodsky, 1981, Hum. Immunol. 3:277-299), and B1.23.2 (anti-HLA-B and -C) (Rebai, N., and B. Malissen, 1983, Tissue Antigens. 22:107-117) was tested by adding a 1/20 dilution of ascites to the test, and it was found that production of TNF was inhibited by mAbs W6/32 (anti-HLA class I) and BB7.2 (anti-HLA-A2), but not by mAb B1.23.2 (anti-HLA-B, -C) (FIG. 2), indicating that the target antigen is presented by HLA-A2. The results of the test are set out in FIG. 2.

Example 2

Identification of the Genes Encoding the Antigen Recognised by CTL 447A/5

Because of the high level expression of almost all the MAGE-A genes in melanoma cell line LB1751-MEL (data not shown), the possibility that CTL 447A/5 recognises an antigen encoded by one of the MAGE-A genes was tested. COS-7 cells were cotransfected with the cDNA of MAGE-A genes cloned in expression vector pcDNAI/Amp together with pcDNAI/Amp-A2, a construct encoding the HLA-A2.1. Transfection was performed by the DEAE-dextran-chloroquine method (Seed, B., et al., 1987, Proc. Natl. Acad. Sci. USA. 84:3365-3369). Briefly, $2 \times 10^4$ COS-7 cells were transfected with 100 ng of plasmid pcDNAI/Amp-A2, a recombinant plasmid containing the HLA-A2.1 gene isolated from a CTL clone of patient SK29 (Wolfel, T., et al., 1993, Int. J. Cancer. 55:237-244), and 100 ng of DNA of MAGE-A genes cloned in pcDNAI/Amp. The transfectants were grown for 48 hours and then tested for their ability to stimulate TNF production by CTL 447A/5 by the method described in Example 1. The tests revealed that a very significant amount of TNF was produced by CTL 447A/5 when stimulated with COS-7 cells transfected with MAGE-A10 DNA. Transfectants with MAGE-A8 cDNA could also stimulate CTL 447A/5 to produce TNF, but less efficiently than those with MAGE-A10 cDNA. No stimulation was observed with COS-7 cells transfected with HLA-A2.1 alone or with the combination of HLA-A2.1 and any of the other MAGE-A genes. The results of these tests are set out in Table 1

TABLE 1

Stimulation of CTL 447A/5 by COS-7 cells transfected with HLA-A2.1 and MAGE-A genes

| Stimulator cells | TNF released by CTL 447A/5 (pg/ml) |
|---|---|
| LB1751-MEL | 28 |
| COS | 7 |
| COS + HLA-A2.1 | 4 |
| COS + HLA-A2.1 + | |
| MAGE-A1 | 3 |
| MAGE-A2 | 4 |
| MAGE-A3 | 4 |
| MAGE-A4 | 4 |
| MAGE-A6 | 4 |
| MAGE-A8 | 30 |
| MAGE-A9 | 3 |
| MAGE-A10 | >120 |
| MAGE-A11 | 4 |
| MAGE-A12 | 2 |

Control stimulator cells included autologous LB1751-MEL, untransfected COS-7 cells, and COS-7 cells transfected only with HLA-A2.1 gene.

Example 3

Identification of the MAGE-A10 Antigenic Peptides

Fragments of different lengths starting from the initiation codon of MAGE-10 (nucleotide 1955 in SEQ. ID. NO. 3) were generated by PCR amplification.

The 1.1-kb open reading frame (ORF) of MAGE-A10 was cloned in plasmid vector pcDNAI/Amp (Invitrogen Corporation, Oxon, UK). Three fragments containing the first 270, 546 and 825 nucleotides of the MAGE-A10 open reading frame (ORF) (nucleotides 1955-3064 in SEQ. ID. No. 3) were amplified by PCR using sense primer 5'-GGAATTCATCAT-GCCTCGAGCTCCAAAGC-3' (SEQ. ID. NO. 51) and three anti-sense primers 5'-GCTCTAGAGCTTAGGCTATCT-GAGCACTCTG-3' (SEQ. ID. NO. 52), 5'-GCTCTA-GAGCTTAGCACTCGGAGGCTTCACT-3' (SEQ. ID. NO. 53), and 5'-GCTCTAGAGCTTACCAATCTTGGGTGAG-CAG-3' (SEQ. ID. NO. 54) respectively. For PCR amplification Pfu DNA polymerase (STRATAGENE, La Jolla, Calif.) was used. A first denaturation step was done for 5 min at 94° C. The first cycle of amplification was performed for 1 min at 94° C. followed by 1 min at 53° C. and 1 min at 72° C., and then additional 25 cycles were performed as follows: 1 min at 94° C., 1 min at 65° C., and 1 min at 72° C. Cycling was concluded with a final extension step of 15 min at 72° C.

The PCR products were digested with EcoRI and Xba I, unidirectionally cloned into the EcoRI and Xba 1 sites of plasmid pcDNAI/Amp and transfected into COS-7 cells together with pcDNAI/Amp-A2, using the DEAE-dextran-chloroquinine method described in Example 2. A CTL stimulation assay was carried out with the transfectants in the manner described in Examples 1 and 2. As shown in FIG. 3, the fragment of 825 bp rendered the transfectants capable of stimulating TNF production by CTL 447A/5, and the 546 bp fragment did not, indicating that the sequence coding for the antigenic peptide is located between nt 547 and 825 of the MAGE-A10 ORF.

In the amino acid sequence corresponding to the nucleotides 547-825 there are two nonapeptides, MLLVFGIDV (codons 183-191 in the ORF) (SEQ. ID. NO. 46) and GLYDGMEHL (254-262) (SEQ. ID. NO. 42), which conform to the HLA-A2.1 peptide binding motif, i.e., a nona- or decapeptide with Leu or Met at position 2 and Leu, Val or Ile at its C-terminus (Rammensee, H. G., et al., 1995, *Immunogenetics*. 41:178-228). These two peptides and their overlapping decapeptides were synthesised on solid phase using F-moc for transient NH$_2$-terminal protection and characterised by mass spectrometry. The peptides were >90% pure, as indicated by analytical HPLC, and used to sensitise autologous lymphoblastoid cell line LB1751-EBV in a chromium release assay as described in (Boon, T., et al., 1980, *J. Exp. Med.* 152:1184-1193) but modified as follows. The target cells were $^{51}$Cr-labeled for 1 h at 37° C. and then washed extensively. 1,000 target cells were then incubated in 96-well microplates in the presence of various concentrations of peptides for 30 min at 37° C. and CTLs were added at an E/T ratio of 20. Chromium release was measured after 4 h at 37° C.

Figure 4A:
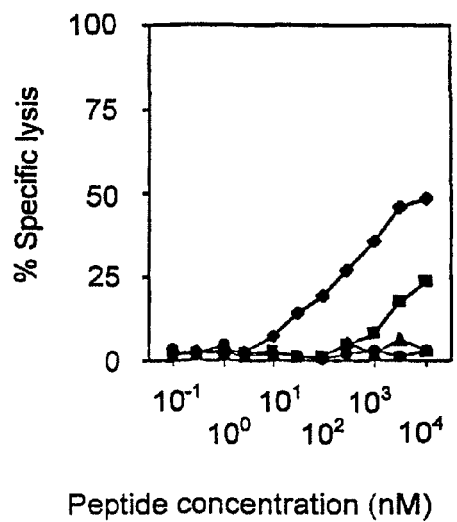
FIG. 4. Shows the extent of lysis by CTL 447A/5 of peptide-sensitised LB1751-EBV cells. (A) LB1751-EBV cells pulsed with peptides derived from MAGE-A10. Chromium-labelled autologous EBV-transformed lymphoblastoid cells LB1751-EBV were pulsed for 30 min with peptides as indicated at various concentrations before addition of CTL 447A/5 at an E/T ratio of 20. Chromium release was measured after 4 h. (B) Enhancement by mAb MA2.1 of lysis of LB 1751-EBV cells pulsed with MAGE-A10 peptides. LB1751-EBV cells were pre-treated with or without anti-HLA-A2 antibody MA2.1. The pre-treatment was performed by adding mAb MA2.1 during $^{51}$Cr-labeling. Peptide sensitisation and chromium release assay were carried out as in (A).
Figure 4B:
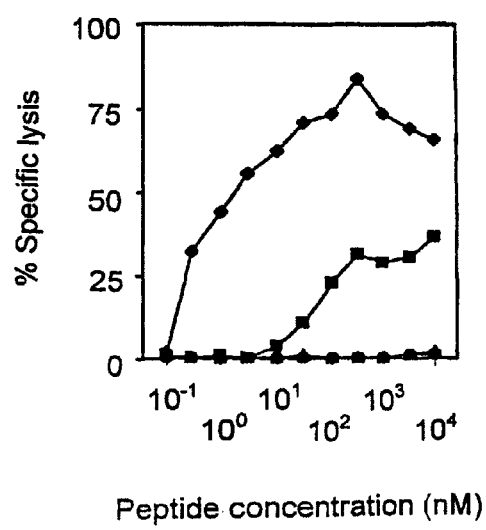

It was found that the nonapeptide GLYDGMEHL (254-262) (SEQ. ID. NO. 42) and, less efficiently, the decapeptide GLYDGMEHLI (254-263) (SEQ. ID. NO. 44), could sensitise LB1751-EBV cells to lysis by CTL 447A/5 (FIG. 4A). When pre-treated with anti-HLA-A2 antibody MA2.1 for 1 h before peptide sensitisation, LB1751-EBV cells pulsed with both peptides showed a significantly increased sensitivity to lysis by the CTL (FIG. 4B). mAb MA2.1 can facilitate the binding of peptides to HLA-A2 molecules on the cell surface, thereby augmenting lysis of peptide-sensitised target cells by HLA-A2-restricted peptide-specific CTL (Bodmer, H., et al., 1989, *Nature* 342:443-446). Enhancement of peptide binding to the HLA-A2 molecule was achieved by incubation of target cells during $^{51}$Cr-labeling with a 1/5 dilution of hybridoma culture supernatant of mAb MA2.1 (McMichael, A. J., et al., 1980, *Hum. Immunol.* 1:121-129; and Bodmer, H., et al., 1989, *Nature* 342:443-446). The other two peptides MLLVF-GIDV (183-191) (SEQ. ID. NO. 46) and CMLLVFGIDV (182-191) (SEQ. ID. NO. 47) failed to confer recognition by the CTLs, even after LB1751-EBV cells were treated with mAb MA2.1.

Example 4

Identification of Mage-A8 Antigen Peptides

Figure 5:
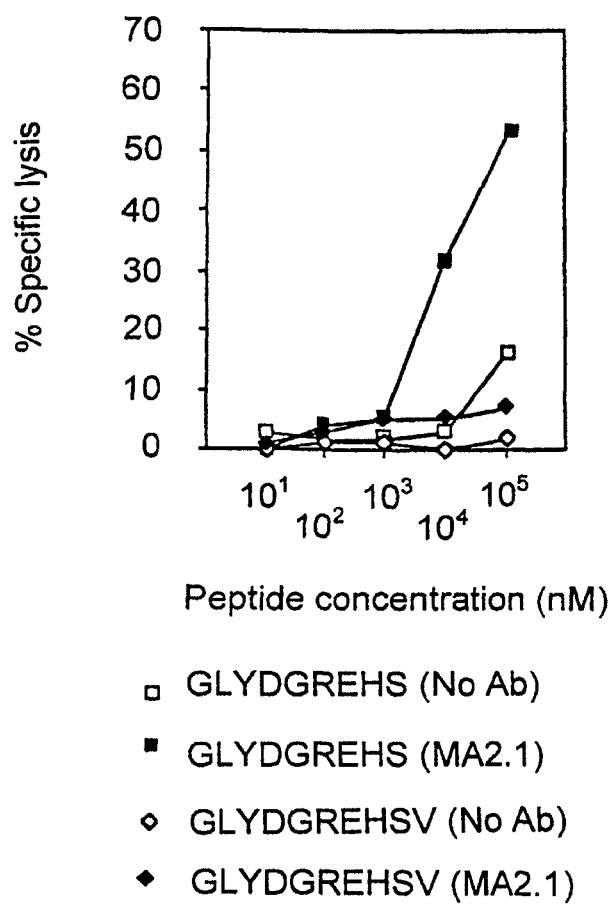
FIG. 5. Shows the extent of lysis by CTL 447A/5 of LB1751-EBV cells sensitised with peptides derived from MAGE-A8. LB1751-EBV cells were pre-treated with or without anti-HLA-A2 antibody MA2.1. Ab treatment and peptide sensitisation of the cells and chromium release assay were carried out as in FIG. 4.

The sequence of MAGE-A8, which is homologous to that of the MAGE-A10 gene encoding GLYDGMEHL (SEQ. ID. NO. 42), codes for peptide GLYDGREHS (codons 232-240 in the MAGE-A8 ORF) (SEQ. ID. NO. 43) that displays two amino acid changes at positions 6 and 9. This peptide and its overlapping decapeptide GLYDGREHSV (codons 232-241) (SEQ. ID. NO. 45) were synthesised by the technique described above. LB1751-EVB cells incubated with either of the peptides, at a concentration of as high as 10 μM peptide, were not lysed by CTL 447A/5. However, when the peptide concentration was increased to 100 μM could GLYDGREHS (SEQ. ID. NO. 43) did sensitise LB1751-EBV cells to lysis (FIG. 5). An enhancement of lysis was observed when the LB1751-EBV cells were pre-treated with mAb MA2.1 and pulsed with GLYDGREHS (SEQ. ID. NO. 43), but not GLYDGREHSV (SEQ. ID. NO. 45). Enhancement of peptide binding to the HLA-A2 molecule was achieved by incubation of target cells during $^{51}$Cr-labeling with a 1/5 dilution of hybridoma culture supernatant of mAb MA2.1 (McMichael, A. J., et al., 1980, *Hum. Immunol.* 1: 121-129; and Bodmer, H., et al., 1989, *Nature* 342:443-446).

Example 5

MAGE-A10+ Allo-Tumours Present the Antigen Recognised by CTL 447A15

Using allogenic HLA-A2+ tumour cell lines that express MAGE-A10 or MAGEA8 as stimulator cells, a CTL stimulation assay of the type described above was performed to assess the TNF production by CTL 447A/5. Melanoma cell lines LB373-MEL and AVL3-MEL were derived from patients LB373 and AVL, respectively, and cultured in Iscove's modified Dulbecco's medium containing 10% FCS. Medullary thyroid carcinoma cell line TT (ATCC® No.: CRL1803) was obtained from the American Type Culture Collection (Rockville, Md.) and maintained in DMEM supplemented with 10% FCS. The results of these assays are set out in FIG. 6 and show that two MAGE-A10+ cell lines LB373-MEL and AVL3-MEL could stimulate CTL 447A/5 to produce TNF, but MAGE-A8+ cell line TT could not. Moreover, AVL3-MEL cells were recognised by CTL 447A/5 less efficiently than LB373-MEL cells, which is consistent with the finding that the transcription level of MAGE-A10 in AVL3-MEL was lower than that in LB373-MEL (Serrano, et, al. manuscript in preparation).

Example 6

MAGE-A10 is Expressed in a Variety of Tumours

As the expression of MAGE-A10 has been studied only in a small number of tumours, a series of 314 tumours of various histological types were tested by RT-PCR with primers ensuring specificity for gene MAGE-A10. Briefly, reverse-transcription-PCR (RT-PCR) was performed to detect the expression of MAGE-A10 in tumour tissues. Total RNA purification and cDNA synthesis were carried out as previously described (Weynants et al. Int. J. Cancer. 56:826-829, 1994). 1/40th of the cDNA produced from 2 μg of total RNA was amplified using sense primer 5'-CACAGAGCAGCACTGAAGGAG-3' (SEQ. ID. NO. 55) and anti-sense primer 5'-CTGGGTAAA-GACTCACTGTCTGG-3' (SEQ. ID. NO. 56), which yielded a 485-bp specific fragment of MAGE-A10. For PCR, a first denaturation step was done for 4 min at 94° and then 30 cycles of amplification were performed as follows: 1 min at 94° C., 1 min at 65° C., and 1 min at 72° C. Cycling was concluded with a final extension step of 15 min at 72° C. As shown in Table 2, MAGE-A10 was expressed in a number of tumours of various histological types. The expression of some other MAGE genes was also examined by RT-PCR. Of the 71 tumour samples expressing MAGE-A10, all but two expressed simultaneously at least one of genes MAGE-A1, A2, A3, A4 and A6 (data not shown).

---

The invention claimed is:

1. An isolated nucleic acid molecule comprising
(a) a nucleotide sequence coding for a polypeptide consisting of an unbroken sequence of amino acids from SEQ ID NO:1 that complexes with a major histocompatibility complex molecule type HLA-A2, wherein the amino acid sequence of said polypeptide is not that set out in either of SEQ ID NOs:1 and 2, or that coded for by nucleotides 334-918 of SEQ ID NO:7, or GLEGAQAPL (SEQ ID NO:50), or FLLFKYQMK (SEQ ID NO:48), or FIEGYCTPE (SEQ ID NO:49), or CLGLSYDGL (SEQ ID NO:57), or
(b) a nucleotide sequence that is fully complimentary to the nucleotide sequence of (a),
wherein the nucleic acid molecule or the nucleotide sequence is not that set out in any of SEQ ID NOs: 3, 4, or 7, and wherein the nucleic acid molecule does not encode the polypeptide set out in either of SEQ ID NOs:1 and 2.

2. The isolated nucleic acid molecule as claimed in claim 1 comprising
(a) an unbroken sequence of nucleotides from SEQ ID NOs: 3 or 4, or
(b) a nucleotide sequence that is fully complimentary to the nucleotide sequence of (a).

3. The isolated nucleic acid molecule as claimed in claim 1, wherein said nucleotide sequence encodes a plurality of epitopes or a polytope.

4. The isolated nucleic acid molecule as claimed in claim 2, wherein said unbroken sequence of nucleotides encodes a plurality of epitopes or a polytope.

5. An isolated nucleic acid molecule comprising
(a) a nucleotide sequence coding for a polypeptide consisting of an unbroken sequence of amino acids from SEQ ID NO:1, wherein either the amino acid following the N-terminal amino acid is L and the C-terminal amino acid is L, V, or I, or the amino acid following the N-terminal amino acid is M and the C-terminal amino acid is I, other than a nonapeptide having the sequence CLGL-SYDGL (SEQ ID NO:57), or GLEGAQAPL (SEQ ID NO:50),
(b) a nucleotide sequence coding for a polypeptide consisting of the amino acid sequence GLYDGMEHL (SEQ ID NO:42) or the amino acid sequence GLYDGMEHLI (SEQ ID NO:44), or
(c) a nucleotide sequence that is fully complimentary to the nucleotide sequence of (a) or (b),
wherein the nucleic acid molecule or the nucleotide sequence is not that set out in any of SEQ ID NOs: 3, 4, or 7, and wherein the nucleic acid molecule does not encode the polypeptide set out in either of SEQ ID NOs:1 and 2.

6. An isolated RNA transcript of the nucleic acid molecule of any of claims 1-5.

7. An isolated expression vector comprising a nucleic acid molecule as claimed in any of claims 1-5 operably linked to a promoter.

8. The isolated expression vector as claimed in claim 7, further comprising a nucleotide sequence coding for a major histocompatibility complex molecule type HLA-A2, preferably HLA-A2.1, a cytokine or a co-stimulatory molecule, or a bacterial or viral genome or a portion thereof.

9. An isolated host cell transformed or transfected with an expression vector as claimed in claim 7.

10. An isolated host cell transformed or transfected with an expression vector as claimed in claim 8.

11. The isolated host cell as claimed in claim 9, transformed or transfected with an expression vector coding for a major histocompatibility complex molecule type HLA-A2, preferably HLA-A2.1, a cytokine or a co-stimulatory molecule.

12. The isolated nucleic acid molecule as claimed in claim 1, wherein the major histocompatibility complex molecule type HLA-A2 is HLA-A2.1.

\* \* \* \* \*

SEQUENCE LISTING

<160> NUMBER OF SEQ ID NOS: 57

<210> SEQ ID NO 1
<211> LENGTH: 369
<212> TYPE: PRT
<213> ORGANISM: Homo sapiens

<400> SEQUENCE: 1

```
Met Pro Arg Ala Pro Lys Arg Gln Arg Cys Met Pro Glu Glu Asp Leu
 1               5                  10                  15

Gln Ser Gln Ser Glu Thr Gln Gly Leu Glu Gly Ala Gln Ala Pro Leu
             20                  25                  30

Ala Val Glu Glu Asp Ala Ser Ser Thr Ser Thr Ser Ser Ser Ser Phe
         35                  40                  45

Pro Ser Ser Phe Pro Ser Ser Ser Ser Ser Ser Ser Ser Ser Cys Tyr
     50                  55                  60

Pro Leu Ile Pro Ser Thr Pro Glu Glu Val Ser Ala Asp Asp Glu Thr
 65                  70                  75                  80

Pro Asn Pro Pro Gln Ser Ala Gln Ile Ala Cys Ser Ser Pro Ser Val
                 85                  90                  95

Val Ala Ser Leu Pro Leu Asp Gln Ser Asp Glu Gly Ser Ser Ser Gln
            100                 105                 110

Lys Glu Glu Ser Pro Ser Thr Leu Gln Val Leu Pro Asp Ser Glu Ser
        115                 120                 125

Leu Pro Arg Ser Glu Ile Asp Glu Lys Val Thr Asp Leu Val Gln Phe
    130                 135                 140

Leu Leu Phe Lys Tyr Gln Met Lys Glu Pro Ile Thr Lys Ala Glu Ile
145                 150                 155                 160

Leu Glu Ser Val Ile Lys Asn Tyr Glu Asp His Phe Pro Leu Leu Phe
                165                 170                 175

Ser Glu Ala Ser Glu Cys Met Leu Leu Val Phe Gly Ile Asp Val Lys
            180                 185                 190

Glu Val Asp Pro Thr Gly His Ser Phe Val Leu Val Thr Ser Leu Gly
        195                 200                 205

Leu Thr Tyr Asp Gly Met Leu Ser Asp Val Gln Ser Met Pro Lys Thr
    210                 215                 220

Gly Ile Leu Ile Leu Ile Leu Ser Ile Ile Phe Ile Glu Gly Tyr Cys
225                 230                 235                 240

Thr Pro Glu Glu Val Ile Trp Glu Ala Leu Asn Met Met Gly Leu Tyr
                245                 250                 255

Asp Gly Met Glu His Leu Ile Tyr Gly Glu Pro Arg Lys Leu Leu Thr
            260                 265                 270

Gln Asp Trp Val Gln Glu Asn Tyr Leu Glu Tyr Arg Gln Val Pro Gly
        275                 280                 285

Ser Asp Pro Ala Arg Tyr Glu Phe Leu Trp Gly Pro Arg Ala His Ala
```

```
            290                 295                 300
Glu Ile Arg Lys Met Ser Leu Leu Lys Phe Leu Ala Lys Val Asn Gly
305                 310                 315                 320

Ser Asp Pro Arg Ser Phe Pro Leu Trp Tyr Glu Glu Ala Leu Lys Asp
                325                 330                 335

Glu Glu Glu Arg Ala Gln Asp Arg Ile Ala Thr Thr Asp Thr Thr
            340                 345                 350

Ala Met Ala Ser Ala Ser Ser Ala Thr Gly Ser Phe Ser Tyr Pro
        355                 360                 365

Glu

<210> SEQ ID NO 2
<211> LENGTH: 234
<212> TYPE: PRT
<213> ORGANISM: Homo sapiens

<400> SEQUENCE: 2

Met Leu Leu Gly Gln Lys Ser Gln Arg Tyr Lys Ala Glu Glu Gly Leu
  1               5                  10                  15

Gln Ala Gln Gly Glu Ala Pro Gly Leu Met Asp Val Gln Ile Pro Thr
            20                  25                  30

Ala Glu Glu Gln Lys Ala Ala Ser Ser Ser Thr Leu Ile Met Gly
        35                  40                  45

Thr Leu Glu Glu Val Thr Asp Ser Gly Ser Pro Ser Pro Gln Ser
 50                  55                  60

Pro Glu Gly Ala Ser Ser Ser Leu Thr Val Thr Asp Ser Thr Leu Trp
 65                  70                  75                  80

Ser Gln Ser Asp Glu Gly Ser Ser Asn Glu Glu Glu Gly Pro Ser
                85                  90                  95

Thr Ser Pro Asp Pro Ala His Leu Glu Ser Leu Phe Arg Glu Ala Leu
            100                 105                 110

Asp Glu Lys Val Ala Glu Leu Val Arg Phe Leu Leu Arg Lys Tyr Gln
            115                 120                 125

Ile Lys Glu Pro Val Thr Lys Ala Glu Met Leu Glu Ser Val Ile Lys
        130                 135                 140

Asn Tyr Lys Asn His Phe Pro Asp Ile Phe Ser Lys Ala Ser Glu Cys
145                 150                 155                 160

Met Gln Val Ile Phe Gly Ile Asp Val Lys Glu Val Asp Pro Ala Gly
                165                 170                 175

His Ser Tyr Ile Leu Val Thr Cys Leu Gly Leu Ser Tyr Asp Gly Leu
            180                 185                 190

Leu Gly Asp Asp Gln Ser Thr Pro Lys Thr Gly Leu Leu Ile Ile Val
            195                 200                 205

Leu Gly Met Ile Leu Met Glu Gly Ser Arg Ala Pro Glu Glu Ala Ile
        210                 215                 220

Trp Glu Ala Leu Ser Val Met Gly Ala Val
225                 230

<210> SEQ ID NO 3
<211> LENGTH: 3510
<212> TYPE: DNA
<213> ORGANISM: Homo sapiens
<220> FEATURE:
<221> NAME/KEY: CDS
<222> LOCATION: (1955)..(3064)

<400> SEQUENCE: 3
```

```
cagggagatg gtggctttgg cgtgcaagac ccatacacga ttcagcagga gggaaaggct    60
gggctgtcgg gagtaaatct gaatacctgg aggacaccca aataaaggaa gtccccgtct   120
tgtccccctc ccctgcccac caccccccc ccccccgcca aatgtctgct ccttctgtca   180
gctttgggaa tcccatgcag gtgtgatcgt gtggtgcccc tccccacttc tgcctgccgg   240
gtctcaggga ggtgaggacc ttggtctgag ggttgctaag aagttattac agggttccac   300
acttggtcaa cagagggagg agtcccagaa tctgcaggac ccaaggggtg ccccctttagt   360
gaggactgga ggtacctgca gcccagaaag aagggatgtc acagagtctg ctgtcccct   420
gttcttagct ctgaggggac ctgatcagga ttggcactaa gtggcaagct caattttacc   480
acaggcagga agatgaggaa ccctcaggga aatggagttt tggtgtaaag gggagatatc   540
agccctggac accccacagg gatgacagga tgtggctcct tcttactttt gttttggaat   600
ctcagggagg tgagaacctt gctctcagag ggtgactcaa gtcaacacag gaacccctc   660
tttttctacag acacagtggg tcgcaggatc tgacaagagt ccaggtaagg aacctgaggg   720
aaatctgagg gtaccccccag cccataacac agatggggtc cccacagaaa tctgccatga   780
ccctactgtc actctggaga acccagtcag ggctgtccgc tgagtctccc tgtcttatac   840
aaggatcact ggtctctggg agggagaggt gttggtctaa gggagctgca ctcgggtcag   900
cagagggagg gtcccagacc ctgccaggag tcaaggtgag gactgagggg acaccattct   960
ccaaacgcac aggactcagc cccaccctac cccttctgtc agccacggga attcatgggg  1020
aactgggggt agatggactc ccctcacttc ctctttccat gtctcctgga ggtaggacct  1080
tggtttaagg aagtggcctc agatcaacaa agggagggtc ccaggtcgta tcaggcatca  1140
agaagaggac caagcaggct cctcacccca gtacacatgg acccagctga atatggccac  1200
ctcttgctgt ctttttctggg aggacctctg cagttgtggc cagatgtggg tcccctcatg  1260
tcttctattt cgtatcaggg atgtaagctt ttgatctgag agtttcttag accagcaaag  1320
gagcagggtc taggctttc caggagaaag gtgagagccc cacgtgagca cagaggctcc  1380
ccaccccagg gtagtgggga actcacagag tccagcccac cctcctgaca acactgggag  1440
gctggggctg tgcttgcagc ctgaaccctg agggcccctc aattcctctt tcaggagctc  1500
cagggactgt gaggtgaggc cttggtctaa ggcagtgttt tcaggtcaca gagcagaaag  1560
ggcccagaca gtgccaggag tcaaggtgag gtgcatgccc tgaatgtgta ccaagggccc  1620
cacctgctcc aggacaaagt ggaccccact gcatcagctc cacctaccct actgtcagtc  1680
ctggagcctt ggcctctgcc ggctgcatcc tgaggagcca tctctcactt ccttcttcag  1740
gttctcaggg gacagggaga gcaagaggtc aagagctgtg gacaccaca gagcagcact  1800
gaaggagaag acctgtaagt tggcctttgt tagaacctcc agggtgtggt tctcagctgt  1860
ggccacttac accctccctc tctccccagg cctgtgggtc cccatcgccc aagtcctgcc  1920
cacactccca cctgctaccc tgatcagagt catc atg cct cga gct cca aag cgt  1975
                                    Met Pro Arg Ala Pro Lys Arg
                                      1               5
cag cgc tgc atg cct gaa gaa gat ctt caa tcc caa agt gag aca cag     2023
Gln Arg Cys Met Pro Glu Glu Asp Leu Gln Ser Gln Ser Glu Thr Gln
         10                  15                  20
ggc ctc gag ggt gca cag gct ccc ctg gct gtg gag gag gat gct tca     2071
Gly Leu Glu Gly Ala Gln Ala Pro Leu Ala Val Glu Glu Asp Ala Ser
      25                  30                  35
tca tcc act tcc acc agc tcc tct ttt cca tcc tct ttt ccc tcc tcc     2119
Ser Ser Thr Ser Thr Ser Ser Ser Phe Pro Ser Ser Phe Pro Ser Ser
 40                  45                  50                  55
```

```
tcc tct tcc tcc tcc tcc tcc tgc tat cct cta ata cca agc acc cca    2167
Ser Ser Ser Ser Ser Ser Ser Cys Tyr Pro Leu Ile Pro Ser Thr Pro
            60                  65                  70 gag gag gtt tct gct gat gat gag aca cca aat cct ccc cag agt gct    2215
Glu Glu Val Ser Ala Asp Asp Glu Thr Pro Asn Pro Pro Gln Ser Ala
        75                  80                  85 cag ata gcc tgc tcc tcc ccc tcg gtc gtt gct tcc ctt cca tta gat    2263
Gln Ile Ala Cys Ser Ser Pro Ser Val Val Ala Ser Leu Pro Leu Asp
            90                  95                  100 caa tct gat gag ggc tcc agc agc caa aag gag gag agt cca agc acc    2311
Gln Ser Asp Glu Gly Ser Ser Ser Gln Lys Glu Glu Ser Pro Ser Thr
        105                 110                 115 cta cag gtc ctg cca gac agt gag tct tta ccc aga agt gag ata gat    2359
Leu Gln Val Leu Pro Asp Ser Glu Ser Leu Pro Arg Ser Glu Ile Asp
120                 125                 130                 135 gaa aag gtg act gat ttg gtg cag ttt ctg ctc ttc aag tat caa atg    2407
Glu Lys Val Thr Asp Leu Val Gln Phe Leu Leu Phe Lys Tyr Gln Met
                140                 145                 150 aag gag ccg atc aca aag gca gaa ata ctg gag agt gtc ata aaa aat    2455
Lys Glu Pro Ile Thr Lys Ala Glu Ile Leu Glu Ser Val Ile Lys Asn
            155                 160                 165 tat gaa gac cac ttc cct ttg ttg ttt agt gaa gcc tcc gag tgc atg    2503
Tyr Glu Asp His Phe Pro Leu Leu Phe Ser Glu Ala Ser Glu Cys Met
        170                 175                 180 ctg ctg gtc ttt ggc att gat gta aag gaa gtg gat ccc act ggc cac    2551
Leu Leu Val Phe Gly Ile Asp Val Lys Glu Val Asp Pro Thr Gly His
            185                 190                 195 tcc ttt gtc ctt gtc acc tcc ggc ctc acc tat gat ggg atg ctg        2599
Ser Phe Val Leu Val Thr Ser Leu Gly Leu Thr Tyr Asp Gly Met Leu
200                 205                 210                 215 agt gat gtc cag agc atg ccc aag act ggc att ctc ata ctt atc cta    2647
Ser Asp Val Gln Ser Met Pro Lys Thr Gly Ile Leu Ile Leu Ile Leu
                220                 225                 230 agc ata atc ttc ata gag ggc tac tgc acc cct gag gag gtc atc tgg    2695
Ser Ile Ile Phe Ile Glu Gly Tyr Cys Thr Pro Glu Glu Val Ile Trp
            235                 240                 245 gaa gca ctg aat atg atg ggg ctg tat gat ggg atg gag cac ctc att    2743
Glu Ala Leu Asn Met Met Gly Leu Tyr Asp Gly Met Glu His Leu Ile
        250                 255                 260 tat ggg gag ccc agg aag ctg ctc acc caa gat tgg gtg cag gaa aac    2791
Tyr Gly Glu Pro Arg Lys Leu Leu Thr Gln Asp Trp Val Gln Glu Asn
            265                 270                 275 tac ctg gag tac cgg cag gtg cct ggc agt gat cct gca cgg tat gag    2839
Tyr Leu Glu Tyr Arg Gln Val Pro Gly Ser Asp Pro Ala Arg Tyr Glu
280                 285                 290                 295 ttt ctg tgg ggt cca agg gct cat gct gaa att agg aag atg agt ctc    2887
Phe Leu Trp Gly Pro Arg Ala His Ala Glu Ile Arg Lys Met Ser Leu
                300                 305                 310 ctg aaa ttt ttg gcc aag gta aat ggg agt gat cca aga tcc ttc cca    2935
Leu Lys Phe Leu Ala Lys Val Asn Gly Ser Asp Pro Arg Ser Phe Pro
            315                 320                 325 ctg tgg tat gag gag gct ttg aaa gat gag gaa gag aga gcc cag gac    2983
Leu Trp Tyr Glu Glu Ala Leu Lys Asp Glu Glu Glu Arg Ala Gln Asp
        330                 335                 340 aga att gcc acc aca gat gat act act gcc atg gcc agt gca agt tct    3031
Arg Ile Ala Thr Thr Asp Asp Thr Thr Ala Met Ala Ser Ala Ser Ser
            345                 350                 355 agc gct aca ggt agc ttc tcc tac cct gaa taa agtaagacag attcttcact  3084
Ser Ala Thr Gly Ser Phe Ser Tyr Pro Glu
360                 365                 370
```

```
gtgttttaaa aggcaagtca ataccacat gattttactc atatgtggaa tctaaaaaaa      3144
aaaaaaaaaa aagttggtat catggaagta gagagtagag cagtagttac attacaatta      3204
aataggagga ataagttcta gtgttctatt gcacagtagg atgactatag ttaacattaa      3264
gatattgtat attacaaaac agctagaagg aaggcttttc aatattgtca ccaaaaagaa      3324
atgataaatg catgaggtga tggatacact acctgatttg atcattatac tacatataca      3384
tgaatcagaa catcaaattg tacctcataa atatctacaa ttacatgtca gttttttgttt     3444 atgttttttgt ttttttttaa tttatgaaaa caaatgagaa tggaaatcaa tgatgtatgt     3504
ggtgga                                                                 3510
```

<210> SEQ ID NO 4
<211> LENGTH: 2559
<212> TYPE: DNA
<213> ORGANISM: Homo sapiens

<400> SEQUENCE: 4

```
tccggggtcg ctcgagccgg ccgggactcg ggatcasaa gtaacggcgg yymkygtkct        60
gagggacagg cttgagatcg gctgaagaga gcgggcccag gctctgtgag gaggcaaggg      120
aggtgagaac cttgctctca gagggtgact caagtcaaca cagggaaccc ctctttttcta     180 cagacacagt gggtcgcagg atctgacaag agtccaggtt tcaggggac agggagagca      240 agaggtcaag agctgtggga caccacagag cagcactgaa ggagaagacc tgcctgtggg      300
tccccatcgc ccaagtcctg cccacactcc cacctgctac cctgatcaga gtcatcatgc      360
ctcgagctcc aaagcgtcag cgctgcatgc ctgaagaaga tcttcaatcc caaagtgaga      420
cacagggcct cgagggtgca caggctcccc tggctgtgga ggaggatgct tcatcatcca      480
cttccaccag ctcctctttt ccatcctctt ttccctcctc ctcctcttcc tcctcctcct      540
cctgctatcc tctaataccca agcacccag aggaggtttc tgctgatgat gagacaccaa      600
atcctcccca gagtgctcag atagcctgct cctcccctcc ggtcgttgct tcccttccat      660
tagatcaatc tgatgagggc tccagcagcc aaaaggagga gagtccaagc accctacagg      720
tcctgccaga cagtgagtct ttacccagaa gtgagataga tgaaaaggtg actgattttgg     780 tgcagtttct gctcttcaag tatcaaaatga aggagccgat cacaaaggca gaaatactgg     840
agagtgtcat aaaaaattat gaagaccact tccctttgtt gtttagtgaa gcctccgagt      900
gcatgctgct ggtctttggc attgatgtaa aggaagtgga tcccactggc cactcctttg      960
tccttgtcac ctcccctgggc ctcacctatg atgggatgct gagtgatgtc cagagcatgc     1020
ccaagactgg cattctcata cttatcctaa gcataatctt catagagggc tactgcaccc      1080
ctgaggaggt catctgggaa gcactgaata tgatgggct gtatgatggg atggagcacc      1140
tcatttatgg ggagcccagg aagctgctca cccaagattg ggtgcaggaa aactacctgg      1200
agtaccggca ggtgcctggc agtgatcctg cacggtatga gtttctgtgg ggtccaaggg      1260
ctcatgctga aattaggaag atgagtctcc tgaaattttt ggccaaggta atgggagtg       1320 atccaagatc cttcccactg tggtatgagg aggcttgaa agatgaggaa gagagagccc      1380
aggacagaat tgccaccaca gatgatacta ctgccatggc cagtgcaagt tctagcgcta      1440
caggtagctt ctcctaccct gaataaagta agacagattc ttcactgtgt tttaaaaggc      1500
aagtcaaata ccacatgatt ttactcatat gtggaatcta aaaaaaaaa aaaaaaaagt      1560 tggtatcatg gaagtagaga gtagagcagt agttacatta caattaaata ggaggaataa      1620
gttctagtgt tctattgcac agtaggatga ctatagttaa cattaagata ttgtatatta      1680
```

-continued

| | |
|---|---|
| caaaacagct agaaggaagg cttttcaata ttgtcaccaa aaagaaatga taaatgcatg | 1740 |
| aggtgatgga tacactacct gatgtgatca ttatactaca tatacatgaa tcagaacatc | 1800 |
| aaattgtacc tcataaatat ctacaattac atgtcagttt ttgtttatgt ttttgttttt | 1860 |
| ttttaattta tgaaacaaa tgagaatgga atcaatgat gtatgtggtg gagggccagg | 1920 |
| ctgaggctga ggaaaataca gtgcataaca tctttgtctt actgttttct ttggataacc | 1980 |
| tggggacttc ttttctttc ttcttggtat tttattttct ttttcttctt cttctttttt | 2040 |
| tttttaaca aagtctcact ctattgctct ggcaggagtg cagtggtgca gtctcggctc | 2100 |
| actgcaactt ccgcctcctg ggttcaagcg attctcctgc ctcagtctcc tgagtagctg | 2160 |
| ggattacaag tgtgcaccac catacccggc taattttgta ttttttagta gagatggggt | 2220 |
| ttcaccatgt tggccaggct ggtctcaaac tcctgacctc aggtaatctg cccgcctcag | 2280 |
| cctcccaaag tgctgggata acaggtgtga gcccactgca ccccagcctc ttcttggtat | 2340 |
| tttaaaatgt tgttactttt actagaatgt ttatgagctt cagaatctaa ggtcacacgt | 2400 |
| tcgtttctgt ttatccagtt taagaaacag ttttgctatt ttgtaaaaca aattgggaac | 2460 |
| ccttccatca tatttgtaat ctttaataaa ataacatgga attggaatag taattttctt | 2520 |
| ggaaatatga aaaatagta aaatagagaa ataattttt | 2559 |

<210> SEQ ID NO 5
<211> LENGTH: 3839
<212> TYPE: DNA
<213> ORGANISM: Homo sapiens
<220> FEATURE:
<221> NAME/KEY: CDS
<222> LOCATION: (2196)..(2900)

<400> SEQUENCE: 5

| | |
|---|---|
| agtctcagat cactggagag aggtgcccca gagcccttaa ggaggactca gcagacctcc | 60 |
| catcatggcc taggaaacct gctcccactc tcaggtctgg gcacccaagg caggacagtg | 120 |
| gggaagggat gtggcccccc cactttctgg tagggggggcc tcaaggagat ggtggccttg | 180 |
| gcatgcaaga cacatccacg gttcagcagg aaggaaaggg ccatgccttg tcgtggagta | 240 |
| aatatgaata cctggatgac acccagacag agaaagaccc catgaaacct actacttctg | 300 |
| tcagccgtgg gaatcccatg cagggttgtc catgtagtgc ctccttactt ctgcctcctg | 360 |
| ggtctcaggg aggtagcaac ctgggtctga agggcgtcct cagctcagca gagggagcca | 420 |
| cacctgttca acagagggac ggggtcacag gatctgcagg acccaagatg tgctcacttt | 480 |
| gtgatgaatg ggggtactcc tggcctggaa agaagggacc ccacaaagtc tggctaactt | 540 |
| tggttattat ctctgggga acccgatcaa gggtggccct aagtggagat ctcatctgta | 600 |
| ctgtgggcag gaagttgggg aaacgcagga agataaggtc ttggtggtaa ggggagatgt | 660 |
| ctgctcatat cagggtgttg tgggttgagg aagggcgggc tccatcaggg gaaagatgaa | 720 |
| taacccctg aagaccttag aacccaccac tcaagaacaa gtagggacag atcctagtgt | 780 |
| cacccctgga cacccaccc agtggtcatc agatgtggtg gctcctcatt tctctcttga | 840 |
| gtctcaggga agtgaggacc ttgttctcag agggcaactc aggacaaaac agggaccccc | 900 |
| atgtgggcaa cagactcagt ggtccaagaa tctaccaaga gtctaggtga caacactgag | 960 |
| ggaagattga gggtaccctc gatggttctc ctagcaggca aaaacagat gggggcccaa | 1020 |
| cagaaatctg cccggcctct tttgtcaccc ctgagagcat gagcaggact atcagctgag | 1080 |
| gcccctgtgt tataccagac tcattggtct caggagaag aaggccttgg tctgagggca | 1140 |
| ctgcattcag gtcagcagag cgggggtcca aggccctgcc aggagtcagg gactcagagg | 1200 |

```
acaccactca ccaaacacac aggaccgaac cccacccotgc accttctgtc agccatggga    1260
agtgcaggga aaggtgggtg gatggaatcc cctcatttgc tcttccagtg tctcctggag    1320
ataggtcctt ggattaagga agtggcctca ggtcagccca ggacacatgg gccccaatgt    1380
attttgtgta gctattgctt ttttctcacc ctaggacaga cacgtgggcc ccattgcatt    1440
ttgtgtagct attgcttttt tcccaggagg ccttgggcat gtggggccag atgtgggtcc    1500
cttcatatcc ttgtcttcca tatcagggat ataaactctt gatctgaaag tttctcaggc    1560
cagcaaaagg gccagatcca ggccctgcca ggagaaagat gagggccctg aatgagcaca    1620
gaaaggacca tccacacaaa atagtgggga gctcacagag tcaggctcac cctcctgaca    1680 gcactgggt gctggggctg tgcttgcagt ctgcagcctg agttcccctc gatttatctt    1740
ctaggagctc caggaaccag gctgtgaggt cttggtctga ggcagtatct tcaatcacag    1800
agcataagag gcccaggcag tagtagcagt caagctgagg tggtgtttcc cctgtatgta    1860
taccagaggc ccctctggca tcagaacagc aggaacccca cagttcctgg ccctaccagc    1920 cctttttgtca gtcctggagc cttggccttt gccaggaggc tgcaccctga gatgccctct    1980
caatttctcc ttcaggttcg cagagaacag gccagccagg aggtcaggag gccccagaga    2040
agcactgaag aagacctgta agtagaacctt tgttagggca tccagggtgt agtacccagc    2100
tgaggcctct cacacgcttc ctctctcccc aggcctgtgg gtctcaattg cccagctccg    2160
gcccacactc tcctgctgcc ctgacctgag tcatc atg ctt ctt ggg cag aag       2213
                                    Met Leu Leu Gly Gln Lys
                                     1               5 agt cag cgc tac aag gct gag gaa ggc ctt cag gcc caa gga gag gca       2261
Ser Gln Arg Tyr Lys Ala Glu Glu Gly Leu Gln Ala Gln Gly Glu Ala
        10                  15                  20 cca ggg ctt atg gat gtg cag att ccc aca gct gag gag cag aag gct       2309
Pro Gly Leu Met Asp Val Gln Ile Pro Thr Ala Glu Glu Gln Lys Ala
    25                  30                  35 gca tcc tcc tcc tct act ctg atc atg gga acc ctt gag gag gtg act       2357
Ala Ser Ser Ser Ser Thr Leu Ile Met Gly Thr Leu Glu Glu Val Thr
40                  45                  50 gat tct ggg tca cca agt cct ccc cag agt cct gag ggt gcc tcc tct       2405
Asp Ser Gly Ser Pro Ser Pro Pro Gln Ser Pro Glu Gly Ala Ser Ser
 55                  60                  65                  70 tcc ctg act gtc acc gac agc act ctg tgg agc caa tcc gat gag ggt       2453
Ser Leu Thr Val Thr Asp Ser Thr Leu Trp Ser Gln Ser Asp Glu Gly
            75                  80                  85 tcc agc agc aat gaa gag gag ggg cca agc acc tcc ccg gac cca gct       2501
Ser Ser Ser Asn Glu Glu Glu Gly Pro Ser Thr Ser Pro Asp Pro Ala
        90                  95                 100 cac ctg gag tcc ctg ttc cgg gaa gca ctt gat gag aaa gtg gct gag       2549
His Leu Glu Ser Leu Phe Arg Glu Ala Leu Asp Glu Lys Val Ala Glu
    105                 110                 115 tta gtt cgt ttc ctg ctc cgc aaa tat caa att aag gag ccg gtc aca       2597
Leu Val Arg Phe Leu Leu Arg Lys Tyr Gln Ile Lys Glu Pro Val Thr
120                 125                 130 aag gca gaa atg ctt gag agt gtc atc aaa aat tac aag aac cac ttt       2645
Lys Ala Glu Met Leu Glu Ser Val Ile Lys Asn Tyr Lys Asn His Phe
135                 140                 145                 150 cct gat atc ttc agc aaa gcc tct gag tgc atg cag gtg atc ttt ggc       2693
Pro Asp Ile Phe Ser Lys Ala Ser Glu Cys Met Gln Val Ile Phe Gly
                155                 160                 165 att gat gtg aag gaa gtg gac cct gcc ggc cac tcc tac atc ctt gtc       2741
Ile Asp Val Lys Glu Val Asp Pro Ala Gly His Ser Tyr Ile Leu Val
        170                 175                 180
```

| | | |
|---|---|---|
| acc tgc ctg ggc ctc tcc tat gat ggc ctg ctg ggt gat gat cag agt<br>Thr Cys Leu Gly Leu Ser Tyr Asp Gly Leu Leu Gly Asp Asp Gln Ser<br>    185                            190                            195 | 2789 |
| acg ccc aag acc ggc ctc ctg ata atc gtc ctg ggc atg atc tta atg<br>Thr Pro Lys Thr Gly Leu Leu Ile Ile Val Leu Gly Met Ile Leu Met<br>    200                            205                           210 | 2837 |
| gag ggc agc cgc gcc ccg gag gag gca atc tgg gaa gca ttg agt gtg<br>Glu Gly Ser Arg Ala Pro Glu Glu Ala Ile Trp Glu Ala Leu Ser Val<br>215                      220                         225                        230 | 2885 |
| atg ggg gct gta tga tgggagggag cacagtgtct attggaagct caggaagctg<br>Met Gly Ala Val<br>              235 | 2940 |
| ctcacccaag agtgggtgca ggagaactac ctggagtacc gccaggcgcc cggcagtgat | 3000 |
| cctgtgcgct acgagttcct gtggggtcca agggcccttg ctgaaaccag ctatgtgaaa | 3060 |
| gtcctggagc atgtggtcag ggtcaatgca agagttcgca tttcctaccc atccctgcat | 3120 |
| gaagaggctt gggagagga gaaggagtt tgagcaggag ttgcagctag gccagtggg | 3180 |
| gcaggttgtg ggagggcctg gccagtgca cgttccaggg ccacatccac cactttccct | 3240 |
| gctctgttac atgaggccca ttcttcactc tgtgtttgaa gagagcagtc acagttctca | 3300 |
| gtagtgggga gcatgttggg tgtgagggaa cacagtgtgg accatctctc agttcctgtt | 3360 |
| ctattgggcg atttggaggt ttatctttgt ttcctttgg aattgttcca atgttccttc | 3420 |
| taatggatgg tgtaatgaac ttcaacattc attttatgta tgacagtaga cagacttact | 3480 |
| gcttttata tagtttagga gtaagagtct tgcttttcat ttatactggg aaacccatgt | 3540 |
| tatttcttga attcagacac tacaagagca gaggattaag gtttttttag aaatgtgaaa | 3600 |
| caacatagca gtaaaataca tgagataaag acataaagaa attaaacaat agttaattct | 3660 |
| tgccttacct gtacctctta gtgtacccta tgtacctgaa tttgcttggc ttctttgaga | 3720 |
| atgaaattga attaaatatg aataaataag tccccctgct cactggctca ttttttccca | 3780 |
| aaatattcat tgagcttccg ctatttggaa ggccctgggt tagtattgga gatgctaca | 3839 |

<210> SEQ ID NO 6
<211> LENGTH: 1810
<212> TYPE: DNA
<213> ORGANISM: Homo sapiens
<220> FEATURE:
<221> NAME/KEY: CDS
<222> LOCATION: (452)..(1153)

<400> SEQUENCE: 6

| | |
|---|---|
| gagctccagg aaccaggctg tgaggtcttg gtctgaggca gtatcttcaa tcacagagca | 60 |
| taagaggccc aggcagtagt agcagtcaag ctgaggtggt gtttcccctg tatgtatacc | 120 |
| agaggcccct ctggcatcag aacagcagga accccacagt tcctggccct accagccctt | 180 |
| ttgtcagtcc tggagccttg gcctttgcca ggaggctgca ccctgagatg ccctctcaat | 240 |
| ttctccttca ggttcgcaga gaacaggcca gccaggaggt caggaggccc cagagaagca | 300 |
| ctgaagaaga cctgtaagta gacctttgtt agggcatcca gggtgtagta cccagctgag | 360 |
| gcctctcaca cgcttcctct ctccccaggc ctgtgggtct caattgccca gctccggccc | 420 |
| acactctcct gctgccctga cctgagtcat c atg ctt ctt ggg cag aag agt<br>                                                       Met Leu Leu Gly Gln Lys Ser<br>                                                         1                    5 | 472 |
| cag cgc tac aag gct gag gaa ggc ctt cag gcc caa gga gag gca cca<br>Gln Arg Tyr Lys Ala Glu Glu Gly Leu Gln Ala Gln Gly Glu Ala Pro<br>      10                       15                      20 | 520 |

```
ggg ctt atg gat gtg cag att ccc aca gct gag gag cag aag gct gca      568
Gly Leu Met Asp Val Gln Ile Pro Thr Ala Glu Glu Gln Lys Ala Ala
         25                  30                  35 tcc tcc tcc tct act ctg atc atg gga acc ctt gag gag gtg act gat      616
Ser Ser Ser Ser Thr Leu Ile Met Gly Thr Leu Glu Glu Val Thr Asp
 40                  45                  50                  55 tct ggg tca cca agt cct ccc cag agt cct gag ggt gcc tcc tct tcc      664
Ser Gly Ser Pro Ser Pro Pro Gln Ser Pro Glu Gly Ala Ser Ser Ser
                 60                  65                  70 ctg act gtc acc gac agc act ctg tgg agc caa tcc gat gag ggt tcc      712
Leu Thr Val Thr Asp Ser Thr Leu Trp Ser Gln Ser Asp Glu Gly Ser
             75                  80                  85 agc agc aat gaa gag gag ggg cca agc acc tcc ccg gac cca gct cac      760
Ser Ser Asn Glu Glu Glu Gly Pro Ser Thr Ser Pro Asp Pro Ala His
         90                  95                 100 ctg gag tcc ctg ttc cgg gaa gca ctt gat gag aaa gtg gct gag tta      808
Leu Glu Ser Leu Phe Arg Glu Ala Leu Asp Glu Lys Val Ala Glu Leu
        105                 110                 115 gtt cgt ttc ctg ctc cgc aaa tat caa att aag gag ccg gtc aca aag      856
Val Arg Phe Leu Leu Arg Lys Tyr Gln Ile Lys Glu Pro Val Thr Lys
120                 125                 130                 135 gca gaa atg ctt gag agt gtc atc aaa aat tac aag aac cac ttt cct      904
Ala Glu Met Leu Glu Ser Val Ile Lys Asn Tyr Lys Asn His Phe Pro
                140                 145                 150 gat atc ttc agc aaa gcc tct gag tgc atg cag gtg atc ttt ggc att      952
Asp Ile Phe Ser Lys Ala Ser Glu Cys Met Gln Val Ile Phe Gly Ile
            155                 160                 165 gat gtg aag gaa gtg gac cct gcc ggc cac tcc tac atc ctt gtc acc     1000
Asp Val Lys Glu Val Asp Pro Ala Gly His Ser Tyr Ile Leu Val Thr
        170                 175                 180 tgc ctg ggc ctc tcc tat gat ggc ctg ctg ggt gat gat cag agt acg     1048
Cys Leu Gly Leu Ser Tyr Asp Gly Leu Leu Gly Asp Asp Gln Ser Thr
185                 190                 195 ccc aag acc ggc ctc ctg ata atc gtc ctg ggc atg atc tta atg gag     1096
Pro Lys Thr Gly Leu Leu Ile Ile Val Leu Gly Met Ile Leu Met Glu
200                 205                 210                 215 ggc agc cgc gcc ccg gag gag gca atc tgg gaa gca ttg agt gtg atg     1144
Gly Ser Arg Ala Pro Glu Glu Ala Ile Trp Glu Ala Leu Ser Val Met
                220                 225                 230 ggg gct gta tgatgggagg gagcacagtg tctattggaa gctcaggaag            1193
Gly Ala Val ctgctcaccc aagagtgggt gcaggagaac tacctggagt accgccaggc gcccggcagt   1253
gatcctgtgc gctacgagtt cctgtggggt ccaagggccc ttgctgaaac cagctatgtg   1313
aaagtcctgg agcatgtggt cagggtcaat gcaagagttc gcatttccta cccatccctg   1373
catgaagagg ctttgggaga ggagaaagga gtttgagcag gagttgcagc tagggccagt   1433
ggggcaggtt gtgggagggc ctgggccagt gcacgttcca gggccacatc caccactttc   1493
cctgctctgt tacatgaggc ccattcttca ctctgtgttt aagagagca gtcacagttc    1553 tcagtagtgg ggagcatgtt gggtgtgagg gaacacagtg tggaccatct ctcagttcct   1613
gttctattgg gcgatttgga ggtttatctt tgtttccttt tggaattgtt ccaatgttcc   1673
ttctaatgga tggtgtaatg aacttcaaca ttcatttat gtatgacagt agacagactt    1733
actgcttttt atatagttta ggagtaagag tcttgctttt catttatact gggaaaccca   1793
tgttatttct tgaattc                                                  1810

<210> SEQ ID NO 7
<211> LENGTH: 920
```

<212> TYPE: DNA
<213> ORGANISM: Homo sapiens
<220> FEATURE:
<221> NAME/KEY: CDS
<222> LOCATION: (334)..(918)

<400> SEQUENCE: 7

```
acctgctcca ggacaaagtg gaccccactg catcagctcc acctacccta ctgtcagtcc       60
tggagccttg gcctctgccg gctgcatcct gaggagccat ctctcacttc cttcttcagg      120
ttctcagggg acaggagag caagaggtca agagctgtgg acaccacag agcagcactg         180 aaggagaaga cctgtaagtt ggcctttgtt agaacctcca gggtgtggtt ctcagctgtg      240
gccacttaca ccctccctct ctccccaggc ctgtgggtcc ccatcgccca agtcctgccc      300
acactcccac ctgctaccct gatcagagtc atc atg cct cga gct cca aag cgt       354
                                    Met Pro Arg Ala Pro Lys Arg
                                      1               5 cag cgc tgc atg cct gaa gaa gat ctt caa tcc caa agt gag aca cag        402
Gln Arg Cys Met Pro Glu Glu Asp Leu Gln Ser Gln Ser Glu Thr Gln
         10                  15                  20 ggc ctc gag ggt gca cag gct ccc ctg gct gtg gag gag gat gct tca        450
Gly Leu Glu Gly Ala Gln Ala Pro Leu Ala Val Glu Glu Asp Ala Ser
     25                  30                  35 tca tcc act tcc acc agc tcc tct ttt cca tcc tct ttt ccc tcc tcc        498
Ser Ser Thr Ser Thr Ser Ser Ser Phe Pro Ser Ser Phe Pro Ser Ser
 40                  45                  50                  55 tcc tct tcc tcc tcc tcc tcc tgc tat cct cta ata cca agc acc cca        546
Ser Ser Ser Ser Ser Ser Ser Cys Tyr Pro Leu Ile Pro Ser Thr Pro
                 60                  65                  70 gag gag gtt tct gct gat gat gag aca cca aat cct ccc cag agt gct        594
Glu Glu Val Ser Ala Asp Asp Glu Thr Pro Asn Pro Pro Gln Ser Ala
             75                  80                  85 cag ata gcc tgc tcc tcc ccc tcg gtc gtt gct tcc ctt cca tta gat        642
Gln Ile Ala Cys Ser Ser Pro Ser Val Val Ala Ser Leu Pro Leu Asp
         90                  95                 100 caa tct gat gag ggc tcc agc agc caa aag gag gag agt cca agc acc        690
Gln Ser Asp Glu Gly Ser Ser Ser Gln Lys Glu Glu Ser Pro Ser Thr
     105                 110                 115 cta cag gtc ctg cca gac agt gag tct tta ccc aga agt gag ata gat        738
Leu Gln Val Leu Pro Asp Ser Glu Ser Leu Pro Arg Ser Glu Ile Asp
120                 125                 130                 135 gaa aag gtg act gat ttg gtg cag ttt ctg ctc ttc aag tat caa atg        786
Glu Lys Val Thr Asp Leu Val Gln Phe Leu Leu Phe Lys Tyr Gln Met
                 140                 145                 150 aag gag ccg atc aca aag gca gaa ata ctg gag agt gtc ata aaa aat        834
Lys Glu Pro Ile Thr Lys Ala Glu Ile Leu Glu Ser Val Ile Lys Asn
             155                 160                 165 tat gaa gac cac ttc cct ttg ttg ttt agt gaa gcc tcc gag tgc atg        882
Tyr Glu Asp His Phe Pro Leu Leu Phe Ser Glu Ala Ser Glu Cys Met
         170                 175                 180 ctg ctg gtc ttt ggc att gat gta aag gaa gtg gat cc                     920
Leu Leu Val Phe Gly Ile Asp Val Lys Glu Val Asp
     185                 190                 195
```

<210> SEQ ID NO 8
<211> LENGTH: 9
<212> TYPE: PRT
<213> ORGANISM: Homo sapiens

<400> SEQUENCE: 8

Glu Ala Asp Pro Thr Gly His Ser Tyr
 1               5

<210> SEQ ID NO 9
<211> LENGTH: 9
<212> TYPE: PRT
<213> ORGANISM: Homo sapiens

<400> SEQUENCE: 9

Ser Ala Tyr Gly Glu Pro Arg Lys Leu
 1               5

<210> SEQ ID NO 10
<211> LENGTH: 9
<212> TYPE: PRT
<213> ORGANISM: Homo sapiens

<400> SEQUENCE: 10

Glu Val Asp Pro Ile Gly His Leu Tyr
 1               5

<210> SEQ ID NO 11
<211> LENGTH: 9
<212> TYPE: PRT
<213> ORGANISM: Homo sapiens

<400> SEQUENCE: 11

Phe Leu Trp Gly Pro Arg Ala Leu Val
 1               5

<210> SEQ ID NO 12
<211> LENGTH: 10
<212> TYPE: PRT
<213> ORGANISM: Homo sapiens

<400> SEQUENCE: 12

Met Glu Val Asp Pro Ile Gly His Leu Tyr
 1               5                   10

<210> SEQ ID NO 13
<211> LENGTH: 9
<212> TYPE: PRT
<213> ORGANISM: Homo sapiens

<400> SEQUENCE: 13

Ala Ala Arg Ala Val Phe Leu Ala Leu
 1               5

<210> SEQ ID NO 14
<211> LENGTH: 8
<212> TYPE: PRT
<213> ORGANISM: Homo sapiens

<400> SEQUENCE: 14

Tyr Arg Pro Arg Pro Arg Arg Tyr
 1               5

<210> SEQ ID NO 15
<211> LENGTH: 10
<212> TYPE: PRT
<213> ORGANISM: Homo sapiens

<400> SEQUENCE: 15

Ser Pro Ser Ser Asn Arg Ile Arg Asn Thr
 1               5                   10

<210> SEQ ID NO 16

```
<211> LENGTH: 9
<212> TYPE: PRT
<213> ORGANISM: Homo sapiens

<400> SEQUENCE: 16

Val Leu Pro Asp Val Phe Ile Arg Cys
1               5

<210> SEQ ID NO 17
<211> LENGTH: 10
<212> TYPE: PRT
<213> ORGANISM: Homo sapiens

<400> SEQUENCE: 17

Val Leu Pro Asp Val Phe Ile Arg Cys Val
1               5                   10

<210> SEQ ID NO 18
<211> LENGTH: 9
<212> TYPE: PRT
<213> ORGANISM: Homo sapiens

<400> SEQUENCE: 18

Glu Glu Lys Leu Ile Val Val Leu Phe
1               5

<210> SEQ ID NO 19
<211> LENGTH: 9
<212> TYPE: PRT
<213> ORGANISM: Homo sapiens

<400> SEQUENCE: 19

Glu Glu Lys Leu Ser Val Val Leu Phe
1               5

<210> SEQ ID NO 20
<211> LENGTH: 10
<212> TYPE: PRT
<213> ORGANISM: Homo sapiens

<400> SEQUENCE: 20

Ala Cys Asp Pro His Ser Gly His Phe Val
1               5                   10

<210> SEQ ID NO 21
<211> LENGTH: 10
<212> TYPE: PRT
<213> ORGANISM: Homo sapiens

<400> SEQUENCE: 21

Ala Arg Asp Pro His Ser Gly His Phe Val
1               5                   10

<210> SEQ ID NO 22
<211> LENGTH: 9
<212> TYPE: PRT
<213> ORGANISM: Homo sapiens

<400> SEQUENCE: 22

Ser Tyr Leu Asp Ser Gly Ile His Phe
1               5

<210> SEQ ID NO 23
<211> LENGTH: 9
<212> TYPE: PRT
<213> ORGANISM: Homo sapiens
```

```
<400> SEQUENCE: 23

Ser Tyr Leu Asp Ser Gly Ile His Ser
 1               5

<210> SEQ ID NO 24
<211> LENGTH: 9
<212> TYPE: PRT
<213> ORGANISM: Homo sapiens

<400> SEQUENCE: 24

Met Leu Leu Ala Val Leu Tyr Cys Leu
 1               5

<210> SEQ ID NO 25
<211> LENGTH: 9
<212> TYPE: PRT
<213> ORGANISM: Homo sapiens

<400> SEQUENCE: 25

Tyr Met Asn Gly Thr Met Ser Gln Val
 1               5

<210> SEQ ID NO 26
<211> LENGTH: 9
<212> TYPE: PRT
<213> ORGANISM: Homo sapiens

<400> SEQUENCE: 26

Ala Phe Leu Pro Trp His Arg Leu Phe
 1               5

<210> SEQ ID NO 27
<211> LENGTH: 9
<212> TYPE: PRT
<213> ORGANISM: Homo sapiens

<400> SEQUENCE: 27

Ser Glu Ile Trp Arg Asp Ile Asp Phe
 1               5

<210> SEQ ID NO 28
<211> LENGTH: 9
<212> TYPE: PRT
<213> ORGANISM: Homo sapiens

<400> SEQUENCE: 28

Tyr Glu Ile Trp Arg Asp Ile Asp Phe
 1               5

<210> SEQ ID NO 29
<211> LENGTH: 15
<212> TYPE: PRT
<213> ORGANISM: Homo sapiens

<400> SEQUENCE: 29

Gln Asn Ile Leu Leu Ser Asn Ala Pro Leu Gly Pro Gln Phe Pro
 1               5                  10                  15

<210> SEQ ID NO 30
<211> LENGTH: 15
<212> TYPE: PRT
<213> ORGANISM: Homo sapiens

<400> SEQUENCE: 30
```

```
Asp Tyr Ser Tyr Leu Gln Asp Ser Asp Pro Asp Ser Phe Gln Asp
 1               5                  10                  15
```

<210> SEQ ID NO 31
<211> LENGTH: 9
<212> TYPE: PRT
<213> ORGANISM: Homo sapiens

<400> SEQUENCE: 31

```
Ala Ala Gly Ile Gly Ile Leu Thr Val
 1               5
```

<210> SEQ ID NO 32
<211> LENGTH: 10
<212> TYPE: PRT
<213> ORGANISM: Homo sapiens

<400> SEQUENCE: 32

```
Glu Ala Ala Gly Ile Gly Ile Leu Thr Val
 1               5                  10
```

<210> SEQ ID NO 33
<211> LENGTH: 9
<212> TYPE: PRT
<213> ORGANISM: Homo sapiens

<400> SEQUENCE: 33

```
Ile Leu Thr Val Ile Leu Gly Val Leu
 1               5
```

<210> SEQ ID NO 34
<211> LENGTH: 9
<212> TYPE: PRT
<213> ORGANISM: Homo sapiens

<400> SEQUENCE: 34

```
Lys Thr Trp Gly Gln Tyr Trp Gln Val
 1               5
```

<210> SEQ ID NO 35
<211> LENGTH: 9
<212> TYPE: PRT
<213> ORGANISM: Homo sapiens

<400> SEQUENCE: 35

```
Ile Thr Asp Gln Val Pro Phe Ser Val
 1               5
```

<210> SEQ ID NO 36
<211> LENGTH: 9
<212> TYPE: PRT
<213> ORGANISM: Homo sapiens

<400> SEQUENCE: 36

```
Tyr Leu Glu Pro Gly Pro Val Thr Ala
 1               5
```

<210> SEQ ID NO 37
<211> LENGTH: 10
<212> TYPE: PRT
<213> ORGANISM: Homo sapiens

<400> SEQUENCE: 37

```
Leu Leu Asp Gly Thr Ala Thr Leu Arg Leu
 1               5                  10
```

```
<210> SEQ ID NO 38
<211> LENGTH: 10
<212> TYPE: PRT
<213> ORGANISM: Homo sapiens

<400> SEQUENCE: 38

Val Leu Tyr Arg Tyr Gly Ser Phe Ser Val
 1               5                  10

<210> SEQ ID NO 39
<211> LENGTH: 9
<212> TYPE: PRT
<213> ORGANISM: Homo sapiens

<400> SEQUENCE: 39

Leu Tyr Val Asp Ser Leu Phe Phe Leu
 1               5

<210> SEQ ID NO 40
<211> LENGTH: 12
<212> TYPE: PRT
<213> ORGANISM: Homo sapiens

<400> SEQUENCE: 40

Lys Ile Ser Gly Gly Pro Arg Ile Ser Tyr Pro Leu
 1               5                  10

<210> SEQ ID NO 41
<211> LENGTH: 9
<212> TYPE: PRT
<213> ORGANISM: Homo sapiens

<400> SEQUENCE: 41

Tyr Met Asp Gly Thr Met Ser Gln Val
 1               5

<210> SEQ ID NO 42
<211> LENGTH: 9
<212> TYPE: PRT
<213> ORGANISM: Homo sapiens

<400> SEQUENCE: 42

Gly Leu Tyr Asp Gly Met Glu His Leu
 1               5

<210> SEQ ID NO 43
<211> LENGTH: 9
<212> TYPE: PRT
<213> ORGANISM: Homo sapiens

<400> SEQUENCE: 43

Gly Leu Tyr Asp Gly Arg Glu His Ser
 1               5

<210> SEQ ID NO 44
<211> LENGTH: 10
<212> TYPE: PRT
<213> ORGANISM: Homo sapiens

<400> SEQUENCE: 44

Gly Leu Tyr Asp Gly Met Glu His Leu Ile
 1               5                  10

<210> SEQ ID NO 45
<211> LENGTH: 10
```

```
<212> TYPE: PRT
<213> ORGANISM: Homo sapiens

<400> SEQUENCE: 45

Gly Leu Tyr Asp Gly Arg Glu His Ser Val
1               5                   10

<210> SEQ ID NO 46
<211> LENGTH: 9
<212> TYPE: PRT
<213> ORGANISM: Homo sapiens

<400> SEQUENCE: 46

Met Leu Leu Val Phe Gly Ile Asp Val
1               5

<210> SEQ ID NO 47
<211> LENGTH: 10
<212> TYPE: PRT
<213> ORGANISM: Homo sapiens

<400> SEQUENCE: 47

Cys Met Leu Leu Val Phe Gly Ile Asp Val
1               5                   10

<210> SEQ ID NO 48
<211> LENGTH: 9
<212> TYPE: PRT
<213> ORGANISM: Homo sapiens

<400> SEQUENCE: 48

Phe Leu Leu Phe Lys Tyr Gln Met Lys
1               5

<210> SEQ ID NO 49
<211> LENGTH: 9
<212> TYPE: PRT
<213> ORGANISM: Homo sapiens

<400> SEQUENCE: 49

Phe Ile Glu Gly Tyr Cys Thr Pro Glu
1               5

<210> SEQ ID NO 50
<211> LENGTH: 9
<212> TYPE: PRT
<213> ORGANISM: Homo sapiens

<400> SEQUENCE: 50

Gly Leu Glu Gly Ala Gln Ala Pro Leu
1               5

<210> SEQ ID NO 51
<211> LENGTH: 29
<212> TYPE: DNA
<213> ORGANISM: Homo sapiens

<400> SEQUENCE: 51
ggaattcatc atgcctcgag ctccaaagc                               29

<210> SEQ ID NO 52
<211> LENGTH: 31
<212> TYPE: DNA
<213> ORGANISM: Homo sapiens

<400> SEQUENCE: 52
```

```
gctctagagc ttaggctatc tgagcactct g                              31

<210> SEQ ID NO 53
<211> LENGTH: 31
<212> TYPE: DNA
<213> ORGANISM: Homo sapiens

<400> SEQUENCE: 53
gctctagagc ttagcactcg gaggcttcac t                              31

<210> SEQ ID NO 54
<211> LENGTH: 31
<212> TYPE: DNA
<213> ORGANISM: Homo sapiens

<400> SEQUENCE: 54
gctctagagc ttaccaatct tgggtgagca g                              31

<210> SEQ ID NO 55
<211> LENGTH: 21
<212> TYPE: DNA
<213> ORGANISM: Homo sapiens

<400> SEQUENCE: 55
cacagagcag cactgaagga g                                         21

<210> SEQ ID NO 56
<211> LENGTH: 23
<212> TYPE: DNA
<213> ORGANISM: Homo sapiens

<400> SEQUENCE: 56
ctgggtaaag actcactgtc tgg                                       23

<210> SEQ ID NO 57
<211> LENGTH: 9
<212> TYPE: PRT
<213> ORGANISM: Homo sapiens

<400> SEQUENCE: 57

Cys Leu Gly Leu Ser Tyr Asp Gly Leu
 1               5
```